(12) United States Patent  
Sugiyama

(10) Patent No.: US 10,117,589 B2
(45) Date of Patent: Nov. 6, 2018

(54) VEHICLE SEAT

(71) Applicant: TS TECH CO., LTD., Asaka-shi, Saitama (JP)

(72) Inventor: Shinji Sugiyama, Tochigi (JP)

(73) Assignee: TS Tech Co., Ltd., Saitama (JP)

( * ) Notice: Subject to any disclaimer, the term of this patent is extended or adjusted under 35 U.S.C. 154(b) by 53 days.

(21) Appl. No.: 15/108,128

(22) PCT Filed: Dec. 25, 2014

(86) PCT No.: PCT/JP2014/084312
§ 371 (c)(1),
(2) Date: Jun. 24, 2016

(87) PCT Pub. No.: WO2015/099040
PCT Pub. Date: Jul. 2, 2015

(65) Prior Publication Data
US 2016/0317047 A1 Nov. 3, 2016

(30) Foreign Application Priority Data

Dec. 27, 2013 (JP) ................. 2013-272375

(51) Int. Cl.
*A61B 5/04* (2006.01)
*A61B 5/0245* (2006.01)
(Continued)

(52) U.S. Cl.
CPC .......... *A61B 5/0245* (2013.01); *A61B 5/0428* (2013.01); *A61B 5/04085* (2013.01);
(Continued)

(58) Field of Classification Search
CPC ........ A61L 5/18; A61L 5/0245; A61L 5/0456; A61L 5/0428; A61L 5/6893;
(Continued)

(56) References Cited

U.S. PATENT DOCUMENTS

2014/0323838 A1* 10/2014 Nishii .................. A61B 5/6891
600/382

FOREIGN PATENT DOCUMENTS

JP 60-52136 U 4/1985
JP 03-29054 U 3/1991
(Continued)

*Primary Examiner* — Mallika D Fairchild
(74) *Attorney, Agent, or Firm* — Drinker Biddle & Reath LLP

(57) ABSTRACT

A vehicle seat includes sheet-shaped sensors configured to detect electric signals associated with the biopotential of a seated passenger, the vehicle seat being configured to remove noise caused due to static electricity to stably measure a bioelectric signal (e.g., heart rate) of the passenger. A seat back includes the sheet-shaped sensors. A cushion pad placed on a seat back frame is covered with a trim cover. Vertically-extending conductive fabric in a belt shape is disposed on an outer surface of the trim cover. The portion where the conductive fabric is disposed has a three-layer structure of the conductive fabric, a skin, and a wadding. A free end of the conductive fabric drawn into the seat back is provided with a J-hook hooked onto a lower frame bridging portion, thus part of the conductive fabric and the lower frame bridging portion contact each other to be electrically conductive with each other.

12 Claims, 20 Drawing Sheets

(51) Int. Cl.
*B60N 2/58* (2006.01)
*A61B 5/00* (2006.01)
*A61B 5/0408* (2006.01)
*A61B 5/0428* (2006.01)
*B60N 2/00* (2006.01)
*B60N 2/64* (2006.01)

(52) U.S. Cl.
CPC .......... *A61B 5/6893* (2013.01); *A61B 5/7203* (2013.01); *B60N 2/002* (2013.01); *B60N 2/58* (2013.01); *B60N 2/643* (2013.01)

(58) Field of Classification Search
CPC ............... A61L 5/04284; A61L 5/0408; A61L 2562/164; A61L 5/7203
See application file for complete search history.

(56) References Cited

FOREIGN PATENT DOCUMENTS

| | | |
|---|---|---|
| JP | 07-329625 A | 12/1995 |
| JP | 2003-070774 A | 3/2003 |
| JP | 2007-301175 A | 11/2007 |
| JP | 2009-050679 A | 3/2009 |
| JP | 2009-172204 A | 8/2009 |

* cited by examiner

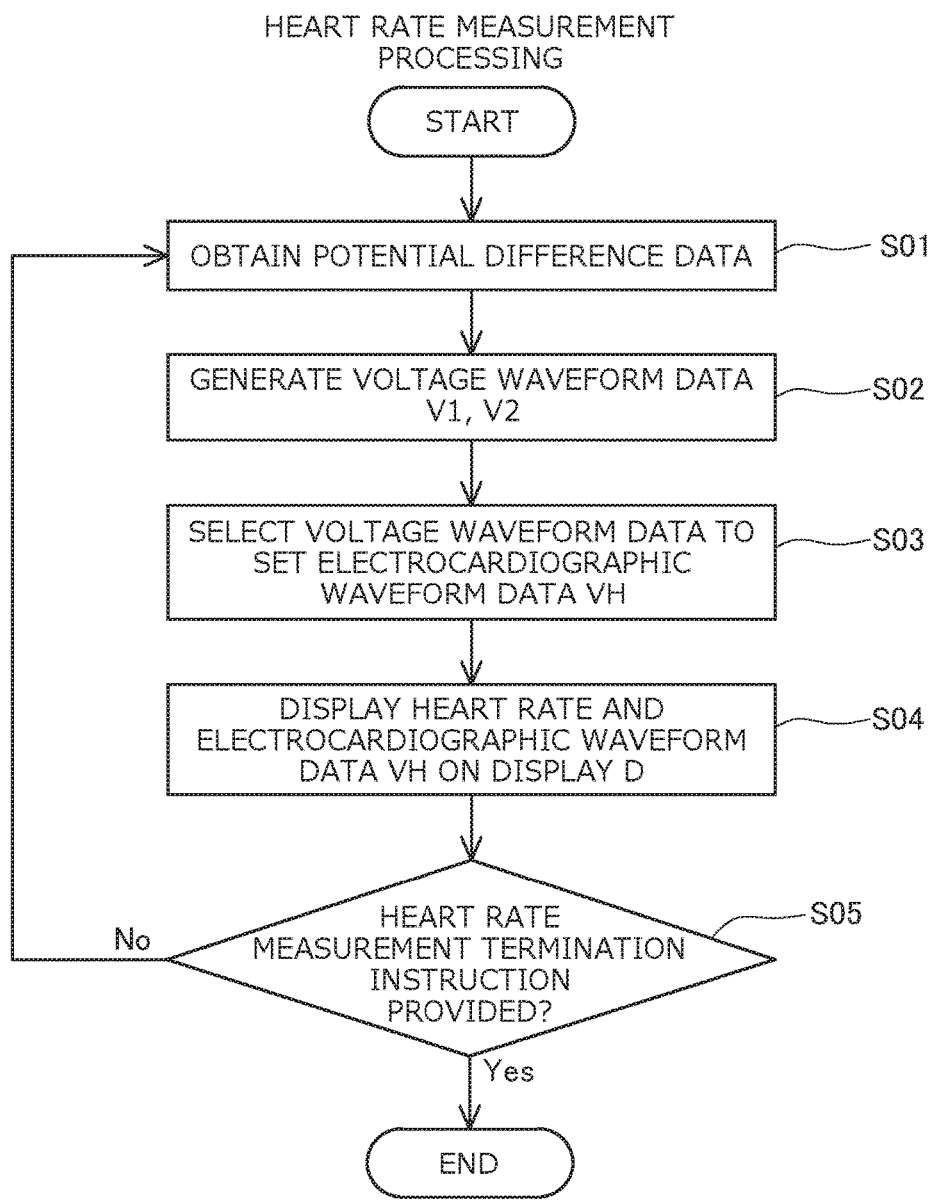

VEHICLE SEAT

CROSS REFERENCE TO RELATED APPLICATIONS

This application is a National Stage Entry application of PCT Application No. PCT/JP2014/084312, filed Dec. 25, 2014, which claims the priority benefit of Japanese Patent Application No. 2013-272375, filed Dec. 27, 2013, the contents being incorporated herein by reference.

BACKGROUND

The present disclosure relates to a vehicle seat, and particularly relates to a vehicle seat that performs a function of measuring the heart rate of a seated passenger.

In recent years, for the purpose of promptly reporting, to a driver, that the driver's physical condition has been changed while a vehicle is running, various vehicle seats capable of displaying a change in physical condition by detecting various parameters indicating the state of the driver have been proposed.

For example, Japanese Patent Publication JP 2009-050679 discloses an electrocardiogram measurement device including first and second electrodes serving as two sensors optionally arranged at a seat back and a ground electrode disposed at a seat cushion and configured to determine a reference potential. In this electrocardiogram measurement device, an electric signal associated with an electrocardiogram detected from a driver by two sensors is efficiently sensed in such a manner that the electric signal is amplified by a two-stage amplifier, and therefore, a driver's health condition can be determined.

Japanese Patent Publication JP 2007-301175 discloses a measurement device including planar electrodes serving as a plurality of sensors arranged respectively at the positions contacting the back of a driver, the region extending from the waist to the hip of the driver, and the thighs of the driver. In this measurement device, one of the sensors is provided for obtaining the neutral-point potential of an amplifier. Thus, abnormality can be determined in such a manner that a electrocardiographic signal and a respiration signal from the driver are suitably detected.

Sheet-shaped sensors have been broadly used, such as the sensors of Japanese Patent Publication JP 2009-050679 and Japanese Patent Publication JP 2007-301175. Each sensor generally includes a conductive line forming a sensor body, and a conductive sheet fixing the conductive line. These sensors are arranged at part of the seat back supporting the back of the seated passenger. When the seated passenger leans on the seat back, the sheet-shaped sensors of this type obtain voltage from the contact portion between the back of the seated passenger and the seat to measure the heart rate.

However, static electricity is caused by slight vibration while the vehicle is running, friction between clothes and the seat back when the seated passenger leans on the seat back, or contact between the seated passenger and, e.g., a steering wheel or a footrest due to movement of the seated passenger in operation. Such static electricity is, as noise, contained in an electrocardiographic waveform. In the vehicle seat including the electrocardiogram measurement device as described in Japanese Patent Publication JP 2009-050679 and Japanese Patent Publication JP 2007-301175, removal and reduction of such static electricity are not taken into consideration. Due to the noise caused by the static electricity, it is difficult to stably detect a bioelectric signal such as an electrocardiographic signal of the seated passenger. For this reason, vital information such as the heart rate might not be able to be accurately measured.

SUMMARY

The present disclosure has been made in view of the above-described problem. Various embodiments of the present disclosure provide a vehicle seat including sheet-shaped sensors configured to detect electric signals associated with a biopotential of a seated passenger, the vehicle seat being configured to remove noise caused due to static electricity to stably measure a bioelectric signal such as an electrocardiographic signal of the seated passenger.

The above-described problem is solved by at least some embodiments of a vehicle seat of the present disclosure. The vehicle seat in an embodiment of the present disclosure is a vehicle seat which includes a seat back configured such that a seat frame having electrical conductivity and a cushion pad are covered with a trim cover, and a sensor attached to the seat back and configured to detect an electric signal associated with the biopotential of a seated passenger, and which is capable of measuring the heart rate of the seated passenger based on the electric signal detected by the sensor. At least part of the trim cover has a multilayer structure in which a conductive member is disposed on an outer surface of the trim cover contacting the seated passenger, and part of the conductive member contacts the seat frame such that the conductive member and the seat frame are in electrical conduction with each other.

In the above-described configuration, part of the trim cover forming the surface of the seat back is provided with the conductive member, and the conductive member contacts the seat frame having the conductivity such that the conductive member and the seat frame are in electrical conduction with each other. With such a configuration, the static electricity caused due to, e.g., friction between the seated passenger and the seat back or the static electricity caused due to various other events can be absorbed by the conductive member contacting the seated passenger, and then, can be released to the seat frame. In the above-described state, since the conductive member provided at the trim cover contacts the seat frame, the seat frame serves as the ground, and as a result, the static electricity caused between the seated passenger and the seat can be efficiently released. Since the static electricity caused between the seated passenger and the seat back is removed (charge control) as described above, the heart rate of the seated passenger can be more stably measured by the sensor attached to the seat back, and a more accurate electrocardiographic waveform can be obtained. Further, since the portion provided with the conductive member is part of the trim cover, a cost is reduced as compared to the case of providing a conductive member across an entire trim cover surface.

At least part of the trim cover is preferably formed of a skin and a wadding material, and the wadding material is preferably disposed between the skin and the sensor. In the above-described configuration, at least part of the trim cover is formed of the skin and the wadding material, and the wadding material is disposed between the skin and the sensor. Thus, wrinkling of the skin can be reduced, and as a result, sensor accuracy is improved.

The conductive member preferably includes conductive fabric, and the conductive fabric is preferably sewn on the skin. Since the conductive fabric is used as the conductive member in the above-described configuration, the layer of the conductive member can be easily formed on the surface of the trim cover by a typical sewing process of covering a wadding material with a skin. Moreover, the conductive fabric and the trim cover can be together drawn into the seat back, and can be grounded as they are. Thus, it is not necessary to additionally use leads such as electric cables, and the conductive fabric can easily contact (i.e., be ground-connected with) the seat frame.

The conductive member is preferably disposed at such a position that the conductive member and the sensor do not overlap with each other. Since the conductive member is disposed at a suitable position in the above-described configuration, a sufficient area contacting the seated passenger can be ensured without interference with the sheet-shaped sensor configured to detect the electric signal, and static electricity can be suitably removed.

The conductive member preferably has a free end on a side contacting the seat frame, and a hook-shaped member is preferably attached to the free end. In the state in which the conductive member is drawn into the seat back, the hook-shaped member is preferably hooked onto the seat frame such that the conductive member and the seat frame contact each other. In the above-described configuration, the hook-shaped member such as a J-hook is attached to the free end as one end of the conductive member, and the conductive member is drawn into the seat back such that the hook-shaped member is hooked onto the seat frame. Thus, the conductive member can easily contact (e.g., be ground-connected with) the seat frame.

The sensor is preferably a capacitance-coupled sheet-shaped sensor. Since the disposed sensor is the capacitance-coupled sheet-shaped sensor in the above-described configuration, voltage is obtained from the contact portion between the back of the seated passenger and the seat so that the heart rate can be suitably measured.

According to an embodiment of the present disclosure, in the vehicle seat including the sheet-shaped sensor configured to detect the electric signal associated with the biopotential of the seated passenger, noise caused due to static electricity can be reduced, and a bioelectric signal such as an electrocardiographic signal of the seated passenger can be more stably measured. According to an embodiment of the present disclosure, wrinkling of the skin can be reduced, and therefore, the sensor accuracy is improved. According to an embodiment of the present disclosure, the conductive member can be attached to the skin by a simple process. According to the present disclosure, static electricity can be more suitably removed. According to an embodiment of the present disclosure, the conductive member and the seat frame can easily contact each other. According to an embodiment of the present disclosure, the heart rate can be suitably measured.

BRIEF DESCRIPTION OF DRAWINGS

Various embodiments of the invention are illustrated in the drawings, in which:

FIG. 13 is a flowchart showing an example of heart rate measurement processing;

DETAILED DESCRIPTION

Embodiments of a vehicle seat of the present disclosure are described in detail below with reference to the drawings. The present disclosure relates to a vehicle seat which includes sheet-shaped sensors attached to a seat back and which can measure the heart rate of a seated passenger based on bioelectric signals of the seated passenger detected by the sheet-shaped sensors. The vehicle seat can remove the noise caused due to static electricity to stably measure the heart rate of the seated passenger. Note that the side on which the passenger is seated on the seat back of the vehicle seat is referred to as a seat front side.

Figure 1:
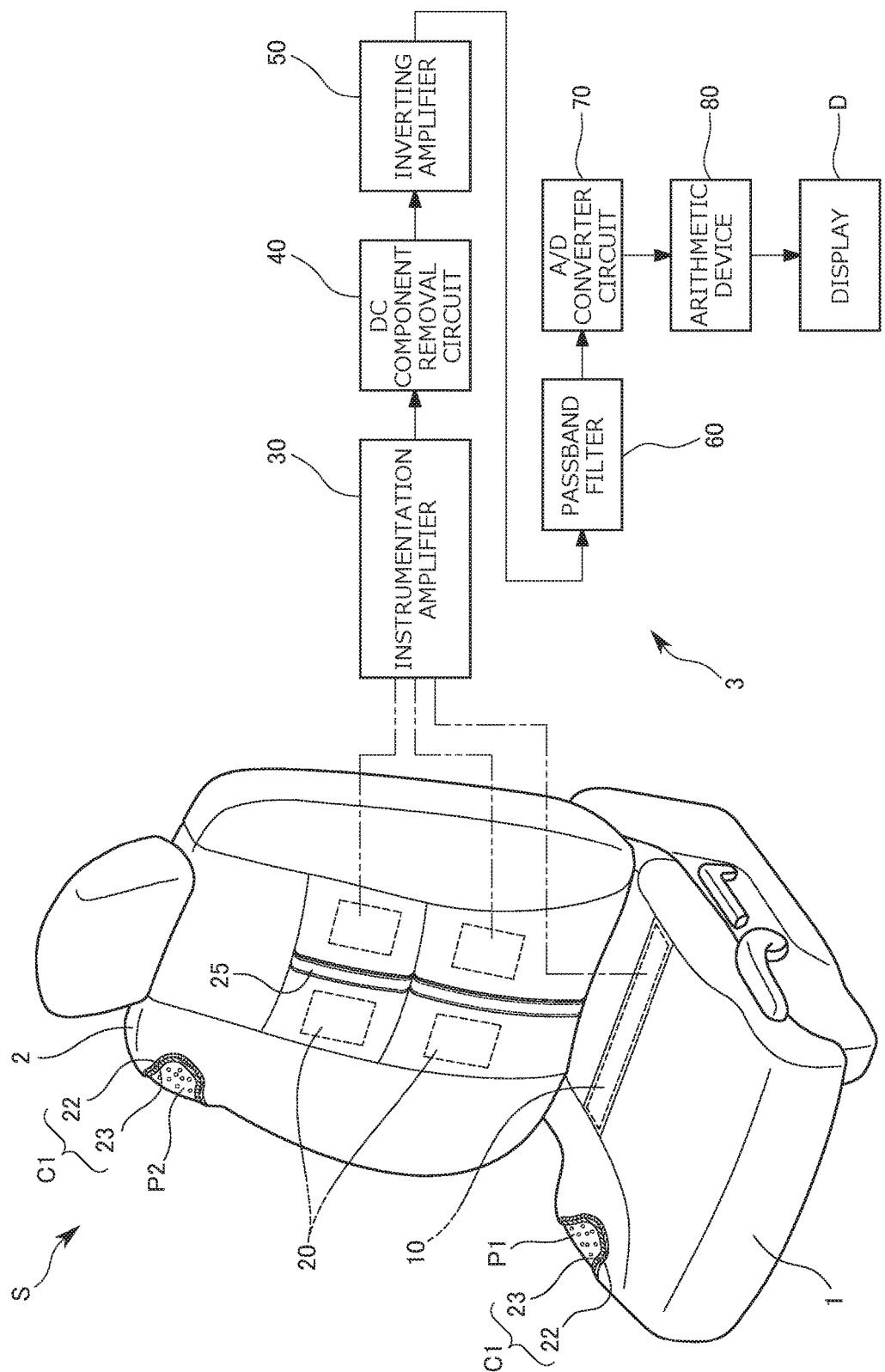
FIG. 1 is a diagram of a configuration of a vehicle seat of an embodiment of the present disclosure.
Figure 2:
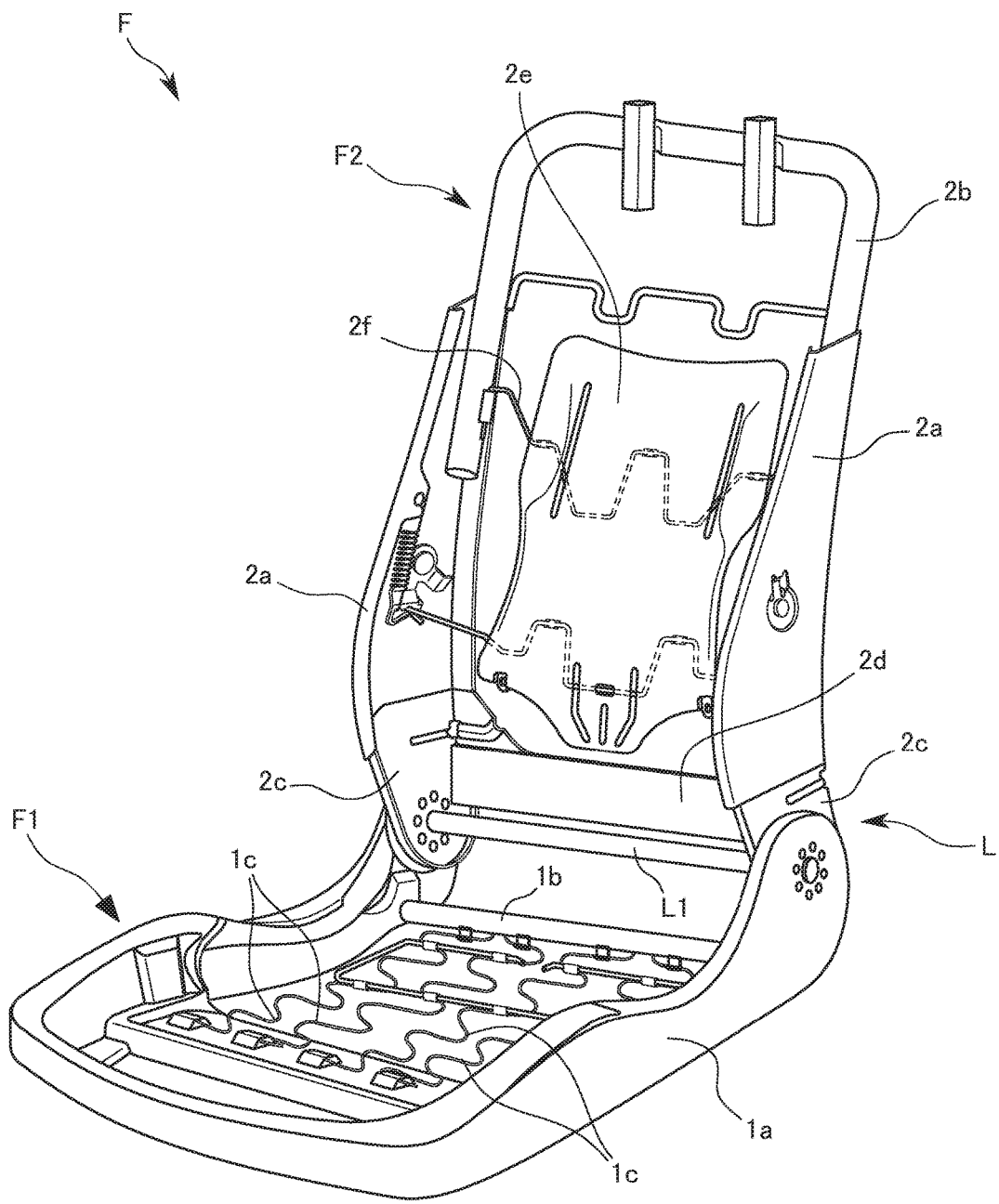
FIG. 2 is a perspective view of a seat frame of the embodiment of the present disclosure.

A vehicle seat S of the present disclosure generally includes, as illustrated in FIGS. 1 and 2, a seat cushion 1 on which a passenger is seated, a seat back 2 rotatably attached to a rear portion of the seat cushion 1 and serving as a backrest of the seated passenger, and a heart rate measurement device 3 including a plurality of sheet-shaped sensors 20 attached to an inside of the seat back 2. Each of the seat cushion 1 and the seat back 2 is configured such that a cushion pad P (P1, P2) is mounted on a seat frame F (F1, F2) and is covered with a trim cover C (C1, C2).

As illustrated in FIG. 2, the seat frame F is a framework of the vehicle seat S, the framework being made of a metal material having electrical conductivity. The seat frame F generally includes the seat cushion frame F1 forming a framework of the seat cushion 1, and the seat back frame F2 forming a framework of the seat back 2. The seat cushion frame F1 and the seat back frame F2 are connected to each other via a reclining mechanism L.

The seat cushion frame F1 generally includes a frame 1a as a substantially U-shaped frame body with an opening on a rear side, a connection pipe 1b as a bridging member for connecting a rear end side of the frame 1a, and S-springs 1c arranged in an inner region surrounded by the frame 1a to support the cushion pad P1 from below. The seat cushion frame F1 is supported by a leg portion (not shown). A not-shown inner rail is attached to the leg portion. The seat cushion frame F1 is slidably assembled such that the position thereof is adjustable back and forth between the inner rail and an outer rail placed on a vehicle body floor.

The seat back frame F2 is a substantially rectangular frame body. The seat back frame F2 generally includes side frames 2a, an upper frame 2b, lower frame bases 2c (member sides), a lower frame bridging portion 2d (a member center), and a pressure receiving member 2e. Since two side frames 2a (the pair of side frames 2a) defines a seat back width, the side frames 2a are extension members arranged separated from each other in a right-left direction of the seat, arranged to extend in a vertical direction of the seat, and forming the side surfaces of the seat back frame F2. The upper frame 2b is a member connecting the upper ends of the pair of side frames 2a, and protrudes upward from the side frames 2a. The upper frame 2b extends upward from one of the side frames 2a, and then, is bent to extend to the other side frame 2a.

The lower frame bases 2c are provided in a pair with a distance in the right-left direction, and each lower frame base 2c is disposed between the seat cushion frame F1 and a corresponding one of the side frames 2a in the height direction of the vehicle seat S. The lower frame bases 2c are connected to the lower side of the side frames 2a, and are formed such that lower portions of the side frames 2a are extended. The lower frame bridging portion 2d is formed to connect the pair of lower frame bases 2c arranged separated from each other in the right-left direction, and is disposed to contact the lower frame bases 2c.

The pressure receiving member 2e is a member disposed in the inner region formed between the side frames 2a and configured to support the cushion pad P2 from the rear side. The pressure receiving member 2e is a member formed in such a manner that resin is formed into a substantially rectangular plate shape. The surface of the pressure receiving member 2e on the side contacting the cushion pad P2 is provided with a smooth raised-recessed portion. The pressure receiving member 2e is hooked onto the side frames 2a via wires 2f, and therefore, is supported by the side frames 2a.

The reclining mechanism L connecting the seat cushion frame F1 and the seat back frame F2 includes at least a reclining shaft L1 provided along the rotation axis of the reclining mechanism L. The reclining shaft L1 is disposed and inserted into shaft insertion holes (not shown) to protrude from the shaft insertion holes toward the side of the seat back frame F2 (more specifically, the pair of side frames 2a), each shaft insertion hole being formed at a corresponding one of the lower frame bases 2c extending downward from the seat back frame F2.

The seat cushion 1 supports the seated passenger from below. As illustrated in FIGS. 1 and 2, the seat cushion 1 is configured such that the cushion pad P1 is placed on the upper side of the seat cushion frame F1 and that the cushion pad P1 and the seat cushion frame F1 are covered with the trim cover C1. A ground electrode 10 is disposed between the cushion pad P1 and the trim cover C1 at a position facing a hip of the seated passenger.

The seat back 2 supports the back of the seated passenger from the rear side. As illustrated in FIGS. 1 and 2, the seat back 2 is configured such that the cushion pad P2 is placed on the seat back frame F2 and that the cushion pad P2 and the seat back frame F2 are covered with the trim cover C2. The plurality of sheet-shaped sensors 20 configured to detect electric signals associated with the biopotential of the seated passenger is arranged between the cushion pad P2 and the trim cover C2 at part of the seat back 2 supporting the back of the seated passenger. The sheet-shaped sensors 20 are described in detail below.

Figure 3:
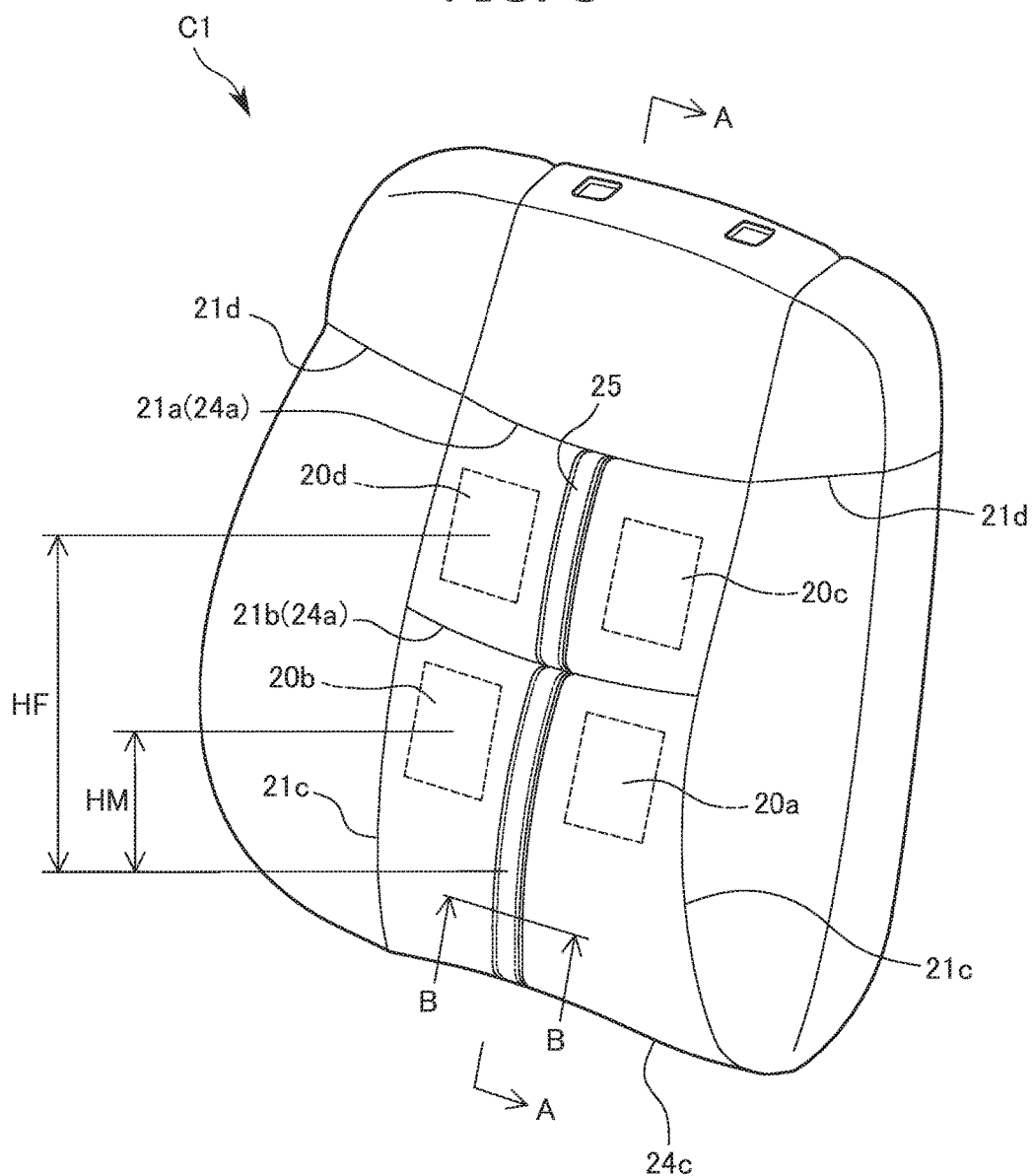
FIG. 3 is a perspective view of a seat back of the embodiment of the present disclosure illustrating the arrangement position of conductive fabric.

As illustrated in FIG. 3, a plurality of insertion grooves 21 is formed on the front side of the cushion pad P2 such that the trim cover C2 is drawn at positions different from the attachment portions of the sheet-shaped sensors 20. Each insertion groove 21 is the groove into which, e.g., an end of the trim cover C2 is drawn. The insertion grooves 21 include two grooves 21a, 21b elongated in the seat width direction and having a substantially rectangular cross section, and two grooves 21c, 21d elongated in the vertical direction and having a substantially rectangular cross section. These grooves are formed at positions different from the sheet-shaped sensors 20.

Note that the following configuration is employed: not-shown through-holes are formed to penetrate the cushion pad P2 in the seat front-rear direction; and distribution cables connected respectively to the sheet-shaped sensors 20 extend to pass through the through-holes from the front side of the cushion pad P2, and are connected to an instrumentation amplifier 30 placed on the rear side of the cushion pad P2. A not-shown cushion slab may be further disposed between the cushion pad P2 to which the sheet-shaped sensors 20 are attached and the trim cover C2. With such a configuration, the sense of discomfort is reduced when the seated passenger leans on the seat back 2.

As illustrated in FIG. 1, the trim cover C covering the seat cushion 1 and the seat back 2 is configured such that a wadding 23 is covered with a skin 22 from the outside. The skin 22 and the wadding 23 are integrated in a multilayer state in such a manner that, e.g., part of the edges of the skin 22 and the wadding 23 are optionally sewn together or bonded together with an adhesive etc.

For example, the following material is employed as the skin 22: a resin sheet material made of, e.g., polyvinyl chloride resin, polyolefin-based resin, or acrylic-based resin; or woven fabric, knitted fabric, or non-woven fabric formed of natural fibers or synthetic fibers. Of the seat cushion 1 and the seat back 2 covered with the trim cover C, the outer surface of the skin 22 is the surface contacting the seated passenger.

The wadding 23 is made of polyvinyl chloride (PVC) foam, olefinic thermoplastic elastomer (TPO) foam, polypropylene (PP) foam, or polyethylene (PE) foam, for example. With the trim cover C provided with the wadding 23, the sense of seating on the seat cushion 1 and the seat back 2 covered with the trim cover C is improved.

Each of the bag-shaped trim covers C1, C2 is formed for a corresponding one of the seat cushion 1 or the seat back 2 in such a manner that a plurality of multilayer parts of the skin 22 and the wadding 23 are sewn together in accordance with the shape of the corresponding one of the seat cushion 1 or the seat back 2. In order to reduce lift-up of the trim cover C and improve the design of the trim cover C, the trim cover C is drawn into end portions or sewn portions 24 thereof. The sewn portions 24 of the trim cover C are at the positions coincident with the insertion grooves 21 formed at the above-described cushion pad P when the seat cushion 1 or the seat back 2 is covered.

Figure 4:
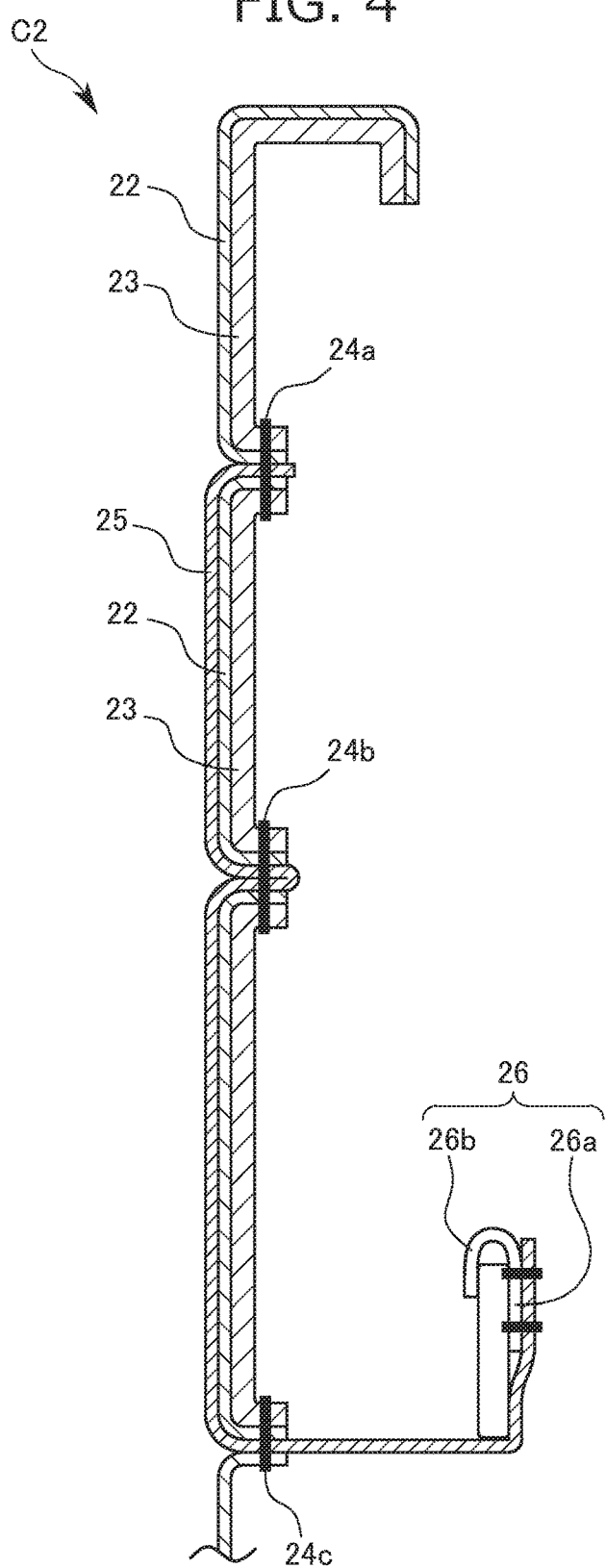
FIG. 4 is an A-A end elevational view of a trim cover covering the seat back illustrated in FIG. 3.
Figure 5:
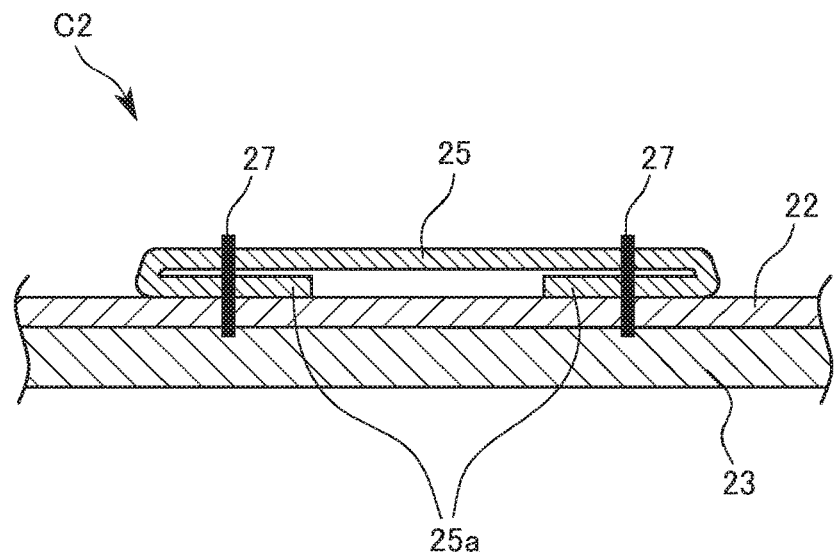
FIG. 5 is a B-B cross-sectional view of the trim cover covering the seat back illustrated in FIG. 3.

In the trim cover C of the present embodiment, conductive fabric 25 as a conductive member is, as illustrated in FIGS. 3 to 5, disposed on an outer surface portion of the skin 22 of the trim cover C2 covering the seat back 2, the outer surface portion contacting the back of the seated passenger. Specifically, the conductive fabric 25 in a belt shape having a width of about 20 mm is, at a substantially center portion of the trim cover C2 in the seat width direction, disposed along the vertical direction connecting between a sewn portion 24a along the transverse insertion groove 21a formed on the upper side and part of a sewn portion 24c formed on the lower side and positioned at a lower end of the seat back 2 when the cushion pad P2 is covered.

The conductive fabric 25 is an elongated belt-shaped member made of a fiber material, the fiber material being formed such that a metal coating film such as copper or nickel is formed on the surface of textile or non-woven fabric formed of, e.g., synthetic fibers of polyester. The conductive fabric 25 exhibits favorable workability in cutting and sewing, favorable flexibility, and favorable elasticity, for example. The conductive fabric 25 made of the above-described material is sewn on an outer surface of the trim cover C2 and the sewn portions 24, and therefore, is disposed with the conductive fabric 25 being integrated with the trim cover C2. Note that the conductive fabric can be easily sewn on the skin 22 and the wadding 23 by a typical known method.

As illustrated in FIG. 4, the A-A end face of the trim cover C2 at the portion where the conductive fabric 25 is disposed, i.e., at the portion between the sewn portion 24a and the sewn portion 24c, shows a three-layer structure of the conductive fabric 25, the skin 22, and the wadding 23 in this order from the outside (e.g., the seating side). Note that no conductive fabric 25 is disposed at the portion above the sewn portion 24a, and therefore, such a portion shows a double-layer structure of the skin 22 and the wadding 23.

The upper end side of the conductive fabric 25 is, together with the skin 22 and the wadding 23, drawn into the insertion groove 21a formed at the cushion pad P2 in the seat back 2 via the sewn portion 24a, and the conductive fabric 25, the skin 22, and the wadding 23 are sewn together at the sewn portion 24a. The conductive fabric 25 extends from the sewn portion 24a in the downward direction of the seat back 2 along the outer surface of the skin 22.

In the middle of extending in the downward direction of the seat back 2, the conductive fabric 25 is, together with the skin 22 and the wadding 23, drawn into the sewn portion 24b positioned between the sewn portion 24a and the sewn portion 24c, i.e., the insertion groove 21b formed substantially in the middle between the insertion groove 21a and the lower end of the seat back 2. In this state, the conductive fabric 25, the skin 22, and the wadding 23 are sewn together at the sewn portion 24b with the conductive fabric 25 being bent in the insertion groove 21b and being pulled out to the outer surface side of the skin 22 again. The conductive fabric 25 further extends from the sewn portion 24b in the downward direction of the seat back 2 along the outer surface of the skin 22.

The conductive fabric 25 is, together with the skin 22 and the wadding 23, drawn into the clearance between the seat back 2 and the seat cushion 1 from a lower end portion of the cushion pad P2, i.e., the position at the lower end of the seat back 2 when the trim cover C2 is attached. The conductive fabric 25, the skin 22, and the wadding 23 are sewn together at the sewn portion 24c in the clearance. The conductive fabric 25 has a bendable free end further extending into the seat back 2 from the sewn portion 24c by a length of about 150 mm to about 200 mm.

A J-hook 26, as a hook-shaped member serving as a hooking tool, is attached to the vicinity of a tip end portion of the free end of the conductive fabric 25. The J-hook 26 includes an attachment portion 26a and a hooking portion 26b, and is attached in such a manner that the attachment portion 26a is sewn on the free end of the conductive fabric 25.

As illustrated in FIG. 5, the conductive fabric 25 is sewn on the skin 22 with sewing threads 27 in the state in which seam allowances 25a formed at both edge portions of the conductive fabric 25 are bent inward (e.g., toward the skin 22) on the outer surface of the skin 22. With such a configuration, the portion where the conductive fabric 25 is disposed on the trim cover C2 shows the three-layer structure of the conductive fabric 25, the skin 22, and the wadding 23 in this order from the outside (e.g., the seating side). Note that in this state, the wadding 23 may be sewn together.

The free end of the conductive fabric 25 drawn into the clearance between the seat back 2 and the seat cushion 1 partially contacts the seat frame F because the J-hook 26 is hooked onto part of the seat frame F. The seat frame F is made of the metal material having conductivity. With such a configuration, the conductive fabric 25 and the seat frame F are in electrical conduction with each other.

Figure 6:
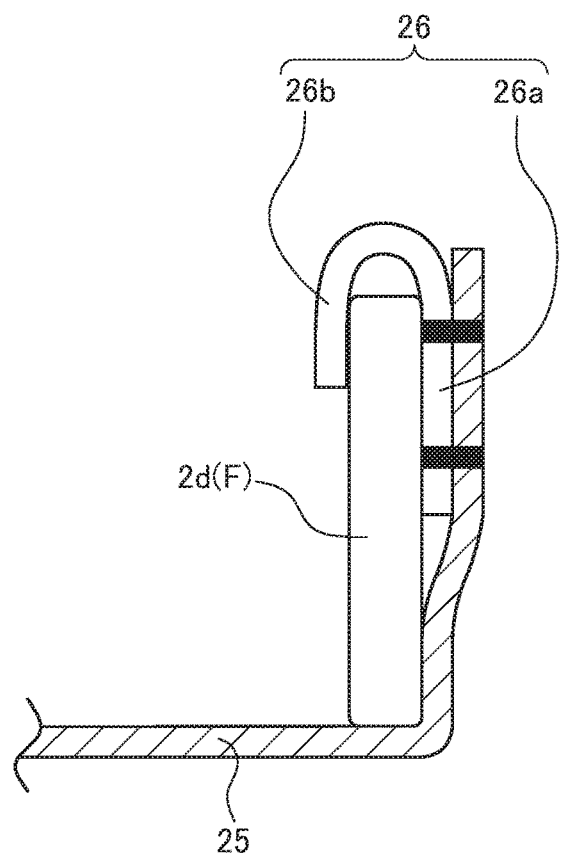
FIG. 6 is an enlarged partial view of a contact portion between the conductive fabric and the seat frame.

Specifically, as illustrated in FIG. 6, the hooking portion 26b of the J-hook 26 is hooked onto an upper end surface of the lower frame bridging portion 2d of the seat back frame F2, part of the conductive fabric 25 contacts the lower frame bridging portion 2d, and the conductive fabric 25 and the lower frame bridging portion 2d are in electrical conduction with each other.

Since the conductive fabric 25 is, as described above, disposed on the surface of the trim cover C2 contacting the seated passenger, the static electricity generated between the seated passenger and the seat back 2 due to, e.g., friction or contact, can be absorbed by the surface contacting the seated passenger. Moreover, since the conductive fabric 25 contacts, at one end thereof, the lower frame bridging portion 2d to be electrically conductive with the lower frame bridging portion 2d, the lower frame bridging portion 2d serves as the ground, and the static electricity absorbed by the conductive fabric 25 is released to the seat back frame F2. That is, the static electricity charged in the seated passenger is released from the portion contacting the seated passenger to the seat back frame F2 through the conductive fabric 25. In this manner, the static electricity is removed.

Note that in the present embodiment, the J-hook 26 is hooked onto the lower frame bridging portion 2d of the seat back frame F2 such that the conductive fabric 25 contacts the lower frame bridging portion 2d, but the contact portion between the conductive fabric 25 and the seat frame F and the method for contacting the conductive fabric 25 and the seat frame F together are not limited to those described above. For example, the member onto which the J-hook 26 is hooked and the member contacting the conductive fabric 25 are not limited to the lower frame bridging portion 2d as in the present embodiment. These members may be any of the seat back frame F2 or the seat cushion frame F1, or may be any member forming the seat frame F.

The J-hook 26 itself may be used as a conductive member to cause the conductive fabric 25 and the seat frame F to be electrically conductive with each other via the J-hook 26 when the J-hook 26 is hooked. The method for contacting the conductive fabric 25 and the seat frame F together may be the method of drawing, together with the trim cover C2, the conductive fabric 25 into, e.g., the seat back frame F2 by a drawing member (not shown) to contact the conductive fabric 25 and the seat back frame F2 together or the method of fixing the conductive fabric 25 to the seat frame F with, e.g., bolts or anchors.

The heart rate measurement device 3 is now described. The heart rate measurement device 3 is configured to detect the bioelectric signals of the seated passenger and measure the heart rate of the seated passenger based on the detected bioelectric signals. As illustrated in FIG. 1, the heart rate measurement device 3 generally includes the ground electrode 10 provided in the seat cushion 1, the sheet-shaped sensors 20 provided in the seat back 2, the instrumentation amplifier 30, a DC component removal circuit 40, an inverting amplifier 50, a passband filter 60, an A/D converter circuit 70, an arithmetic device 80, and a display D.

The ground electrode 10 is formed of a conductive fabric tape, and is configured to obtain a reference potential when an offset signal contained in the bioelectric signal detected by each sheet-shaped sensor 20 is removed. The ground electrode 10 is disposed at part of the seat cushion 1 facing the hip of the seated passenger. The ground electrode 10 is capacitance-coupled to the body of the seated passenger via the trim cover C1 and cloths, and thereby configured to detect the bioelectric signals of the seated passenger. The ground electrode 10 is, using a ground electrode cable, electrically connected to the instrumentation amplifier 30 via a resistor.

Figure 7:
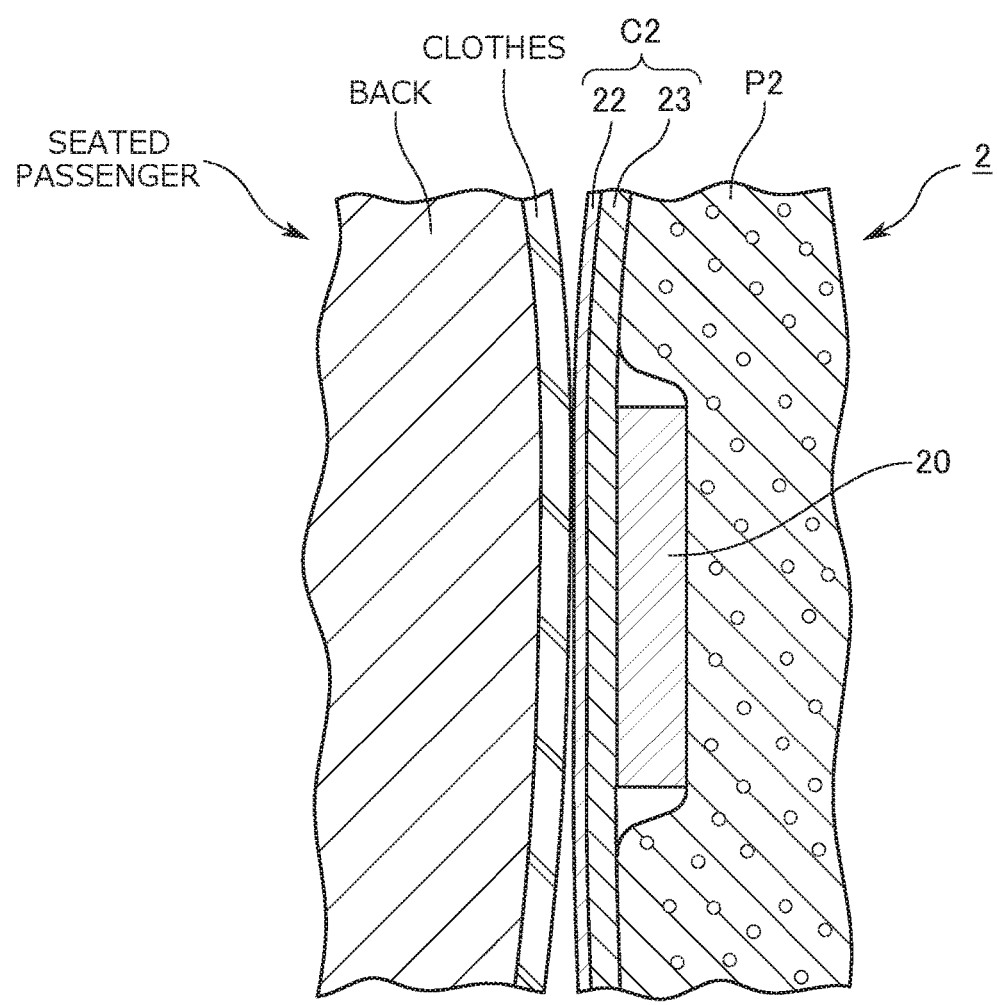
FIG. 7 is a partial cross-sectional view of the seat back illustrating the contact portion between a seated passenger and a sheet-shaped sensor.

Each sheet-shaped sensor 20 is formed of a conductive fabric tape. As illustrated in FIG. 7, each sheet-shaped sensor 20 is the sensor capacitance-coupled to the body of the seated passenger via the trim cover C and the cloths to detect the electric signals associated with the biopotential of the seated passenger. As illustrated in FIG. 3, the plurality of sheet-shaped sensors 20 are bonded to the front side of the cushion pad P2 forming the seat back 2. In the present embodiment, the sheet-shaped sensors 20 include first and second sensors 20a, 20b arranged in the substantially middle of the cushion pad P2 in the seat width direction, and third and fourth sensors 20c, 20d arranged above the first and second sensors 20a, 20b. On the rear side of the cushion pad P2 (the seat back 2), each sheet-shaped sensor 20 is electrically connected to the instrumentation amplifier 30 via a not-shown distribution cable, and the bioelectric signals detected by the sheet-shaped sensors 20 are transmitted to the instrumentation amplifier 30.

Note that the bonding position of each sheet-shaped sensor 20 is preferably such a position that the sheet-shaped sensor 20 does not overlap with the above-described conductive fabric 25 when the cushion pad P2 is covered with the trim cover C2. For example, in the present embodiment, the conductive fabric 25 is disposed between the first and second sensors 20a, 20b bonded to the cushion pad P2 and between the third and fourth sensors 20c, 20d bonded to the cushion pad P2. As long as the sheet-shaped sensors 20 and the conductive fabric 25 do not overlap with each other, a sufficient area contacting the seated passenger can be ensured without interference between each sheet-shaped sensor 20 and the conductive fabric 25. Moreover, while static electricity is suitably removed, the bioelectric signals can be detected.

Moreover, each sheet-shaped sensor 20 is preferably disposed at the position different from the portions provided with the insertion grooves 21. As long as the sheet-shaped sensors 20 and the insertion grooves 21 are arranged at different positions, there is no interference among the sheet-shaped sensors 20 and the insertion grooves 21 when the cushion pad P2 is covered with the trim cover C2. Thus, the ends of the trim cover C2 can be efficiently drawn into the insertion grooves 21.

Figure 8:
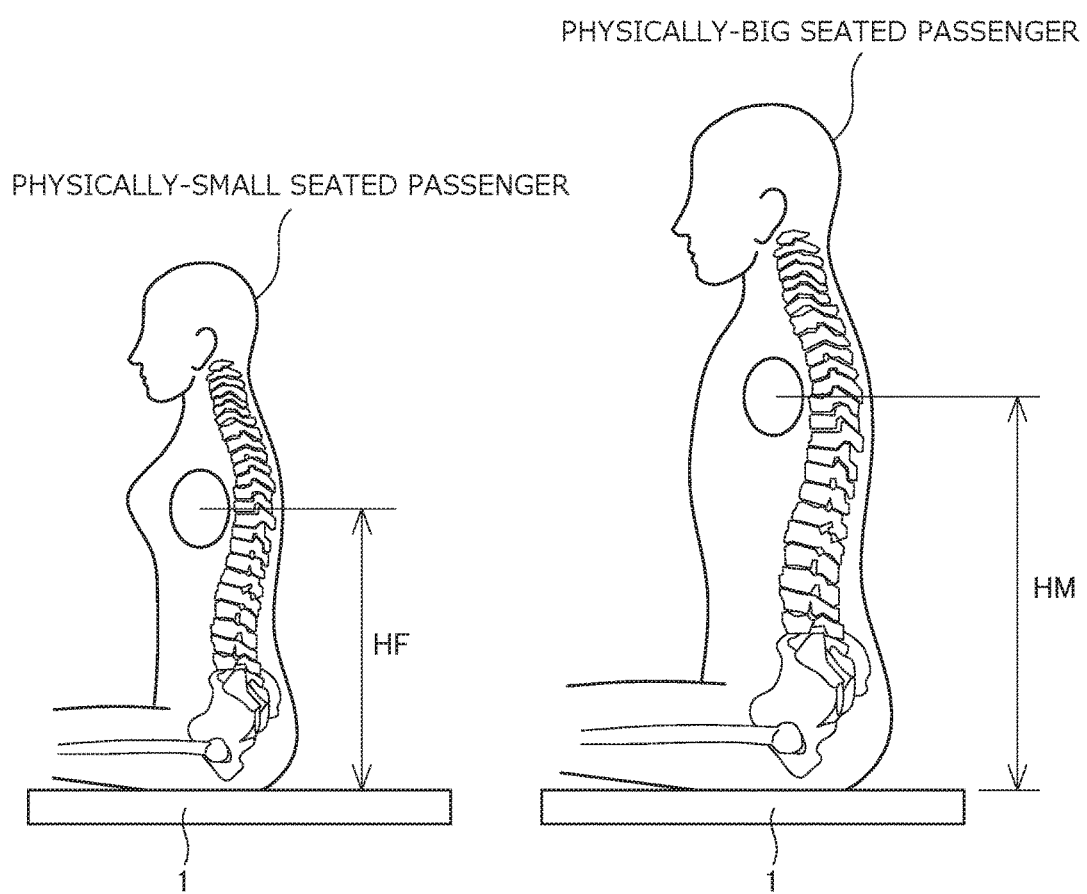
FIG. 8 is a diagram for describing the difference in the height of the heart due to a physique difference.

The height positions of the sheet-shaped sensors 20 attached to the cushion pad P2 is described with reference to FIGS. 3 and 8. First, a physically-small female and a physically-big male are illustrated in FIG. 8 as examples of seated passengers with a physique difference. Suppose that the female assumed as the physically-small seated passenger has a height of about 150 cm, and the male assumed as the physically-big seated passenger has a height of about 190 cm. When seated on the seat cushion 1, the heart of the female is at a height HF from a cushion seating surface corresponding to an upper surface of the seat cushion 1, and the heart of the male is at a height HM from the cushion seating surface. The height HF is about 37 cm in the case of the female with a height of about 150 cm, and the height HM is about 55 cm in the case of the male with a height of about 190 cm.

For the sheet-shaped sensors 20 attached to the seat back 2, arrangement in the height direction is set depending on a heart position difference caused due to the physique difference. Specifically, as illustrated in FIG. 3, the first sensor 20a and the second sensor 20b are arranged such that the height of the center between the first sensor 20a and the second sensor 20b from the cushion seating surface corresponds to the height HF of the heart of the female. Moreover, the third sensor 20c and the fourth sensor 20d are arranged such that the height of the center between the third sensor 20c and the fourth sensor 20d from the cushion seating surface corresponds to the height HM of the heart of the male.

Of the sheet-shaped sensors 20 arranged as described above, the left first sensor 20a and the right second sensor 20b as viewed from the seated passenger are arranged to sandwich the heart of the female in the oblique direction. The region defined to include the first sensor 20a at a lower left corner and to include the second sensor 20b at an upper right corner is a region where a suitable potential difference is obtained in detection of the cardiac potential of the female. Similarly, the left third sensor 20c and the right fourth sensor 20d as viewed from the seated passenger are arranged to sandwich the heart of the male in the oblique direction. The region defined to include the third sensor 20c at a lower left corner and to include the fourth sensor 20d at an upper right corner is a region where a suitable potential difference is obtained in detection of the cardiac potential of the male.

Typically, the heart-induced electric vector produced in expansion/contraction of the heart of a person points in the direction substantially from the right shoulder to the left leg. The sensors are in such arrangement that the direction connecting between the second sensor 20b and the first sensor 20a or the direction connecting between the fourth sensor 20d and the third sensor 20c is along the direction of the heart-induced electric vector. With the above-described arrangement of the sheet-shaped sensors 20, larger potential difference signals (potential difference signals associated with an R-wave in an electrocardiogram) generated in association with contraction of the heart are detected.

In the present embodiment, the conductive fabric 25 disposed to vertically extend between the first sensor 20a and the second sensor 20b and between the third sensor 20c and the fourth sensor 20d contacts the vicinity of the spine of the seated passenger via the clothes to suitably remove the static electricity charged in the seated passenger. Thus, noise due to the static electricity can be removed, and as a result, the bioelectric signals of the seated passenger can be more accurately obtained.

Figure 9:
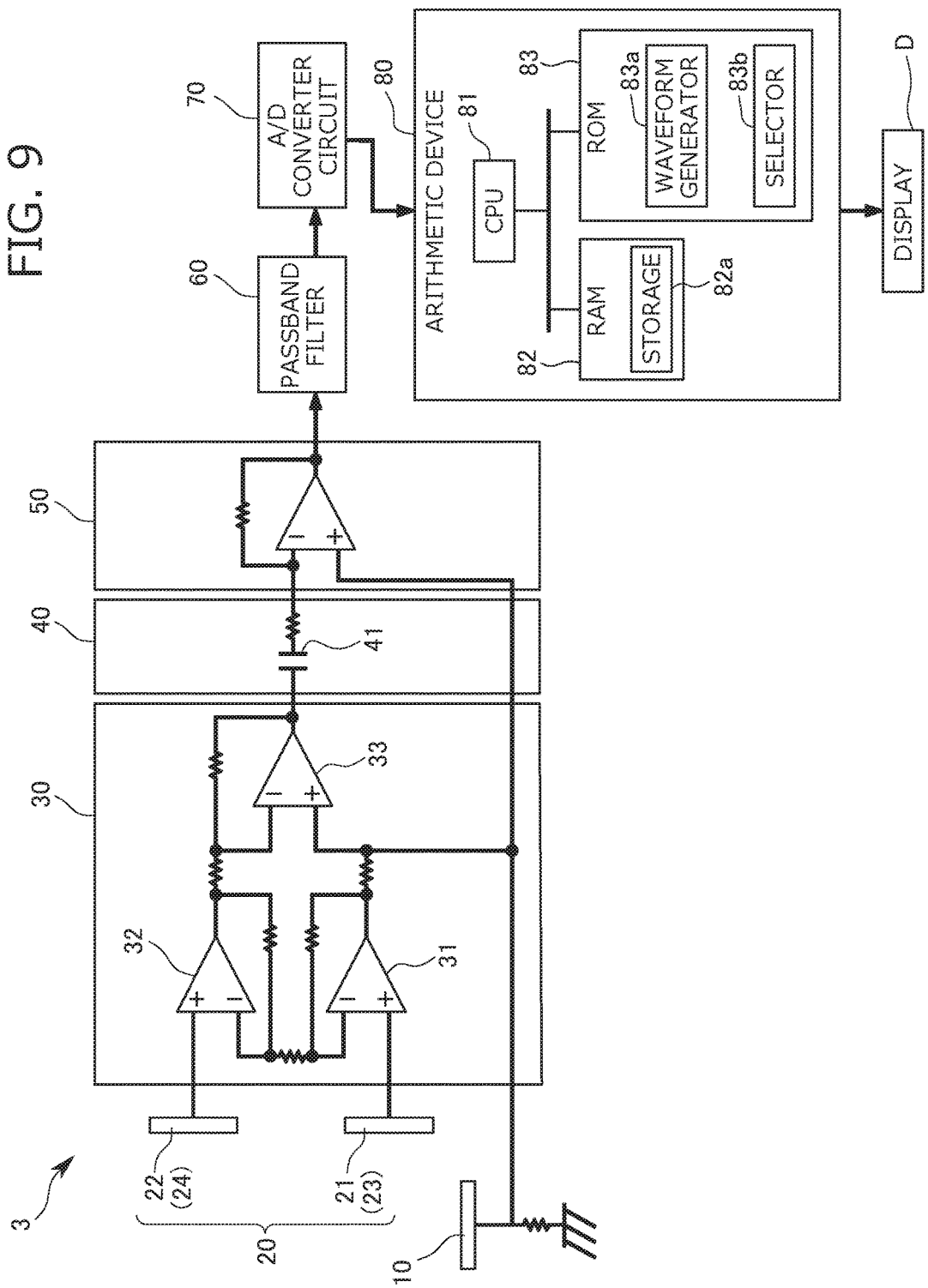
FIG. 9 is a schematic diagram of a circuit configuration for electrocardiographic signal detection and an arithmetic device configuration.

Next, the circuit configuration for electrocardiographic signal detection and the configuration of the arithmetic device are described with reference to FIG. 9. The instrumentation amplifier 30 includes operational amplifiers 31, 32, 33. The operational amplifiers 31, 32 are each configured to amplify the bioelectric signals detected by the sheet-shaped sensors 20 to output the signals to the operational amplifier 33.

The operational amplifier 33 is a differential amplifier, and is configured to amplify a difference signal of the bioelectric signals output from the operational amplifiers 31, 32. The potential of the ground electrode 10 is, as a reference potential, applied to a positive input terminal of the operational amplifier 33. The ground electrode 10 is provided at the seat cushion 1 farther from the heart of the seated passenger than the sheet-shaped sensors 20 provided at the seat back 2, and is capacitance-coupled to the hip of the seated passenger. Thus, a potential that is less susceptible to an electrocardiographic signal is obtained from the ground electrode 10.

A capacitor 41 serving as the DC component removal circuit 40 is configured to remove a low-frequency component, including a direct-current component, of the potential difference signal output from the operational amplifier 33, and AC-couples an output terminal of the operational amplifier 33 and a negative input terminal of the inverting amplifier 50 together.

The inverting amplifier 50 is configured to invert, for further amplification, the polarity of the potential difference signal from which the direct-current component is removed. The negative input terminal of the inverting amplifier 50 is connected to the capacitor 41 via a resistor, and the potential of the ground electrode 10 is applied to a positive input terminal of the inverting amplifier 50 as a reference potential.

The passband filter 60 is provided to remove, from the potential difference signal output from the inverting amplifier 50, a low-frequency component and a high-frequency component, these components being not taken as the frequency of the electrocardiographic signal. The passband filter 60 inputs, in a restrictive manner, the potential difference signal having the frequency of the electrocardiographic signal to the A/D converter circuit 70.

The A/D converter circuit 70 is configured to convert, as an input signal of the arithmetic device 80, an analog signal input from the inverting amplifier 50 via the passband filter 60 into a digital signal.

The arithmetic device 80 includes a CPU 81 for arithmetic control, a random access memory (RAM) 82, and a read only memory (ROM) 83. The signal input to the arithmetic device 80 is the potential difference signal converted into the digital signal as described above, and the signal output from the arithmetic device 80 is the electric signal to be displayed on the display D.

The RAM 82 is configured to temporarily store the parameters containing the signal being in the arithmetic control and the input and output signals, and has a function as a storage 82a configured to store the potential difference signal converted into the digital signal and other signals.

The ROM 83 is configured to store the program to be executed by the CPU 81 and parameters of predetermined values. The ROM 83 stores, as programs, a waveform generator 83a configured to generate voltage waveform data from the potential difference signal obtained from the sheet-shaped sensors 20 and a selector 83b configured to select voltage waveform data periodically oscillating in association with contraction of the heart.

Figure 10A:
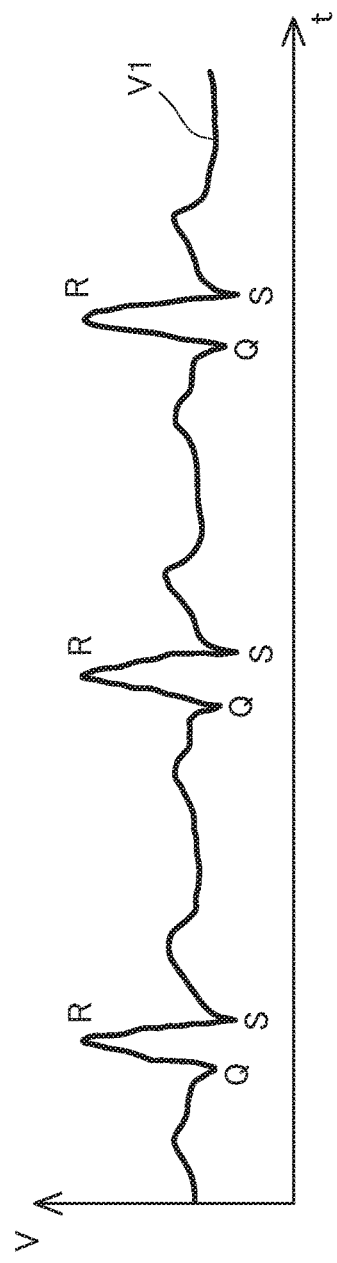
FIGS. 10A and 10B are graphs showing examples of detected electrocardiographic waveform data.
Figure 10B:
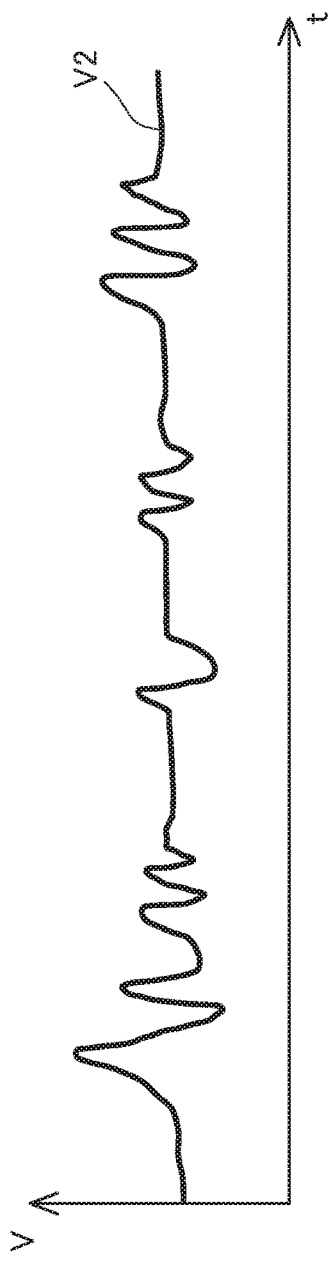

The waveform generator 83a is configured to generate voltage waveform data V1 as shown in FIG. 10A based on the potential difference signal, stored in the storage 82a, between the first sensor 20a and the second sensor 20b, provided that the potential difference signal is represented by the vertical axis V and the time is represented by the horizontal axis t. The waveform generator 83a is further configured to generate voltage waveform data V2 as shown in FIG. 10B based on the potential difference signal between the third sensor 20c and the fourth sensor 20d, provided that the potential difference signal is represented by the vertical axis V and the time is represented by the horizontal axis t.

The selector 83b is configured to select, from the voltage waveform data V1, V2, the voltage waveform data associated with contraction of the heart to set such data as electrocardiographic waveform data VH. Suppose that the voltage waveform data V1 shown in FIG. 10A is generated based on the potential difference signal between the first sensor 20a and the second sensor 20b and that the voltage waveform data V2 shown in FIG. 10B is generated based on the potential difference signal between the third sensor 20c and the fourth sensor 20d. In this case, the selector 83b selects the voltage waveform data V1 clearly showing a periodic R-wave and having a high amplitude to set the voltage waveform data V1 as the electrocardiographic waveform data VH.

It is often the case that the voltage waveform data V1, V2 generated as described above and the selected electrocardiographic waveform data VH typically contain various types of noise. In particular, noise due to static electricity caused by slight vibration while a vehicle is running, friction between the clothes and the seat back when the seated passenger leans on the seat back, or contact between the seated passenger and, e.g., a steering wheel or a footrest due to movement of the seated passenger in operation is noticeable. In the present embodiment, the conductive fabric 25 is disposed at the trim cover C2 covering the seat back 2 to ground and remove the static electricity. Thus, the noise caused due to the static electricity and contained in the voltage waveform data V1, V2 and the electrocardiographic waveform data VH can be suitably removed without, e.g., special arithmetic processing in the heart rate measurement device 3.

Figure 11A:
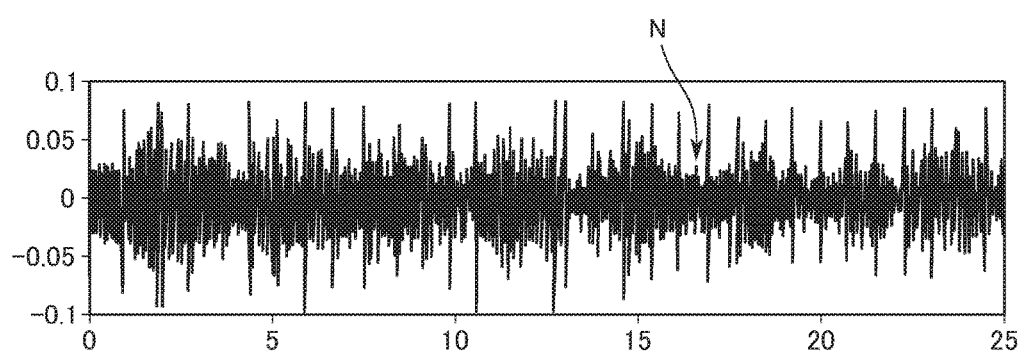
FIGS. 11A and 11B are graphs showing a comparative example of the electrocardiographic waveform data.
Figure 11B:
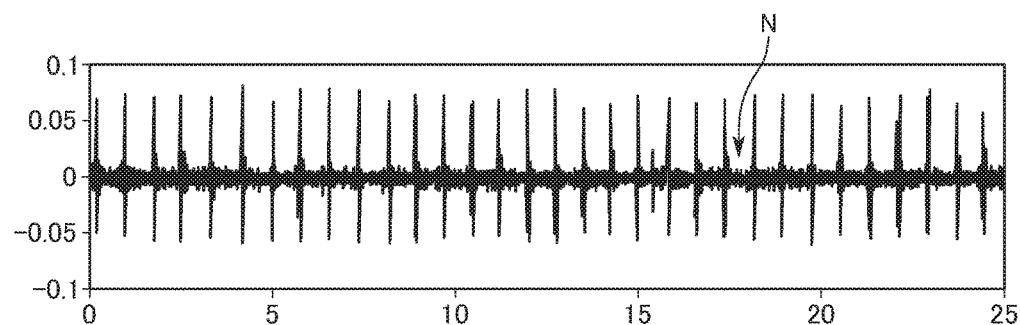

For example, when static electricity is caused due to slight vibration while the vehicle is running or friction between the seated passenger (the clothes) and the seat back, if there is, as in the typical case, no function to remove the static electricity, the noise N caused due to such static electricity is contained in the electrocardiographic waveform data VH, resulting in a waveform shown in FIG. 11A. With the above-described contained noise N, it might be difficult to accurately read the electrocardiographic waveform of the R-wave, for example.

On the other hand, since the static electricity is removed by the conductive fabric 25, the electrocardiographic waveform data VH of the present embodiment as shown in FIG.

11B shows that the noise N caused due to the static electricity and contained in the electrocardiographic waveform is substantially removed.

Figure 12A:
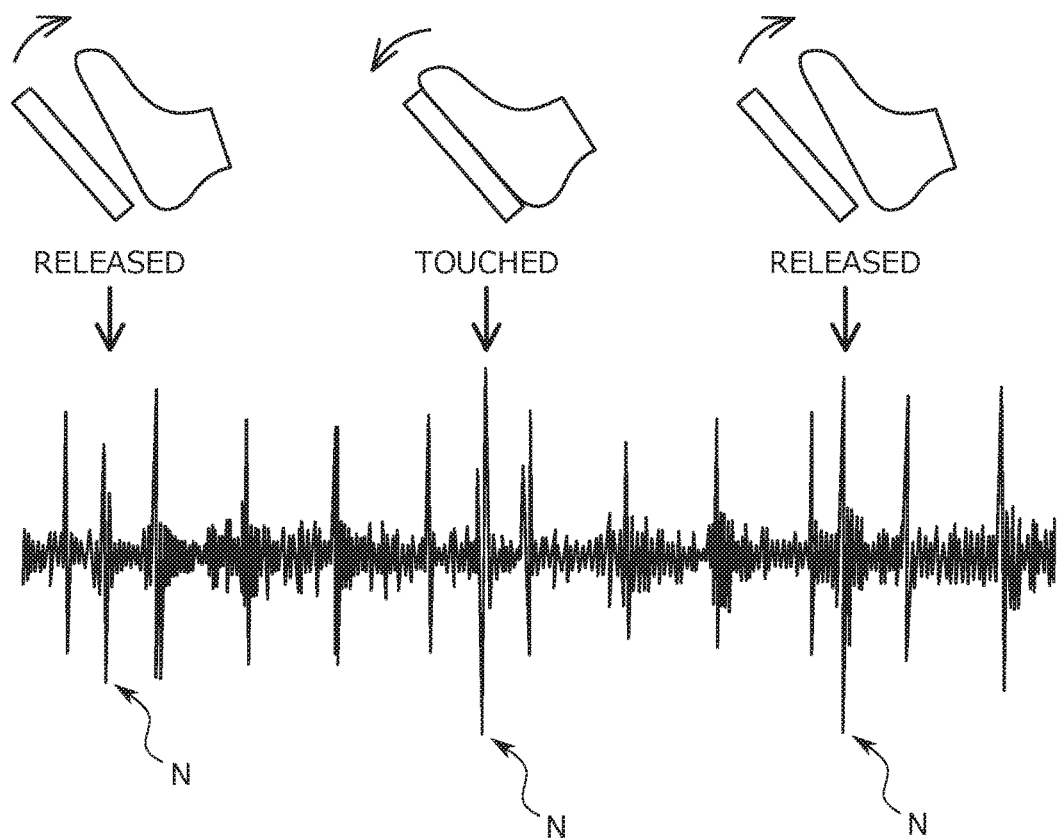
FIGS. 12A and 12B are diagrams showing another comparative example of the electrocardiographic waveform data.

In the case where static electricity is, as shown in FIG. 12A, caused when the foot of the seated passenger touches the footrest or is released from the footrest, if there is, as in the typical case, no function to remove the static electricity, significant noise N which may be confused with the R-wave is contained in the electrocardiographic waveform data VH due to the static electricity. With the above-described contained noise N, it might be difficult to accurately read the electrocardiographic waveform of the R-wave, for example.

Figure 12B:
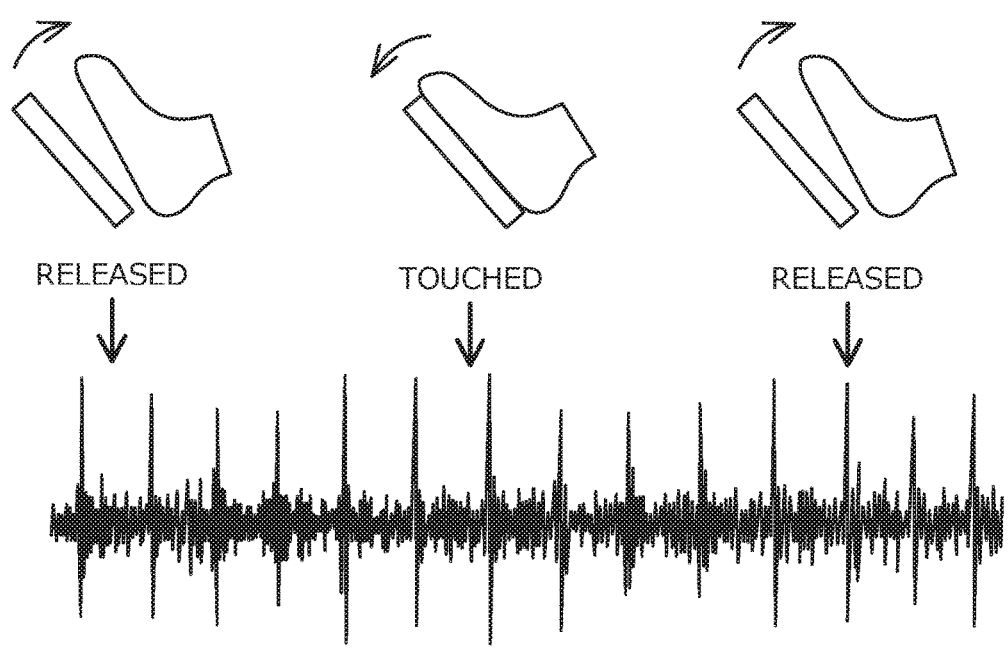

On the other hand, since the static electricity is removed by the conductive fabric 25, the electrocardiographic waveform data VH of the present embodiment as shown in FIG. 12B shows that the noise N caused due to the static electricity and contained in the electrocardiographic waveform is much removed.

Heart Rate Measurement Processing

Next, a heart rate measurement method by the heart rate measurement device 3 is described with reference to FIG. 13. In response to start of an engine of the vehicle or pressing of a start switch, the sheet-shaped sensors 20 detect electric signals associated with the biopotential of the seated passenger from the body of the seated passenger.

The bioelectric signals detected by the first sensor 20a and the second sensor 20b are, as potential difference data, stored in the storage 82a of the arithmetic device 80 via the instrumentation amplifier 30, the DC component removal circuit 40, the inverting amplifier 50, the passband filter 60, and the A/D converter circuit 70. Similarly, the bioelectric signals detected by the third sensor 20c and the fourth sensor 20d are also stored as potential difference data. That is, the arithmetic device 80 obtains the potential difference data between the first sensor 20a and the second sensor 20b and the potential difference data between the third sensor 20c and the fourth sensor 20d (step S01).

Next, based on the obtained potential difference data between the first sensor 20a and the second sensor 20b, the waveform generator 83a generates the voltage waveform data V1 plotted using a potential difference and a time as axes. Similarly, based on the potential difference data between the third sensor 20c and the fourth sensor 20d, the voltage waveform data V2 is generated (step S02).

Next, the selector 83b selects, from two pieces of voltage waveform data V1, V2, the data synchronized with the heart rate and having a high R-wave amplitude, thereby setting the selected data as electrocardiographic waveform data VH (step S03).

Next, the arithmetic device 80 digitally filters the electrocardiographic waveform data VH to emphasize the waveform associated with a QRS-wave, and then, computes a peak interval at which the voltage (an R-wave potential) exceeding a set threshold is detected. The arithmetic device 80 further calculates the number of detection per minute, the inverse of the peak interval being taken as an instantaneous heart rate (the number of heart beat per second). That is, the arithmetic device 80 calculates the heart rate by computing. Next, the arithmetic device 80 transmits the signals associated with the electrocardiographic waveform data VH and the heart rate to the display D, and then, the electrocardiographic waveform data VH and the heart rate are displayed on the display D (step S04).

Next, the arithmetic device 80 determines the presence or absence of the instruction of terminating heart rate measurement by, e.g., a stop switch (step S05). With the instruction of terminating the heart rate measurement, the processing is terminated. Without the instruction, steps S01 to S05 are repeated.

Second Embodiment

Figure 14:
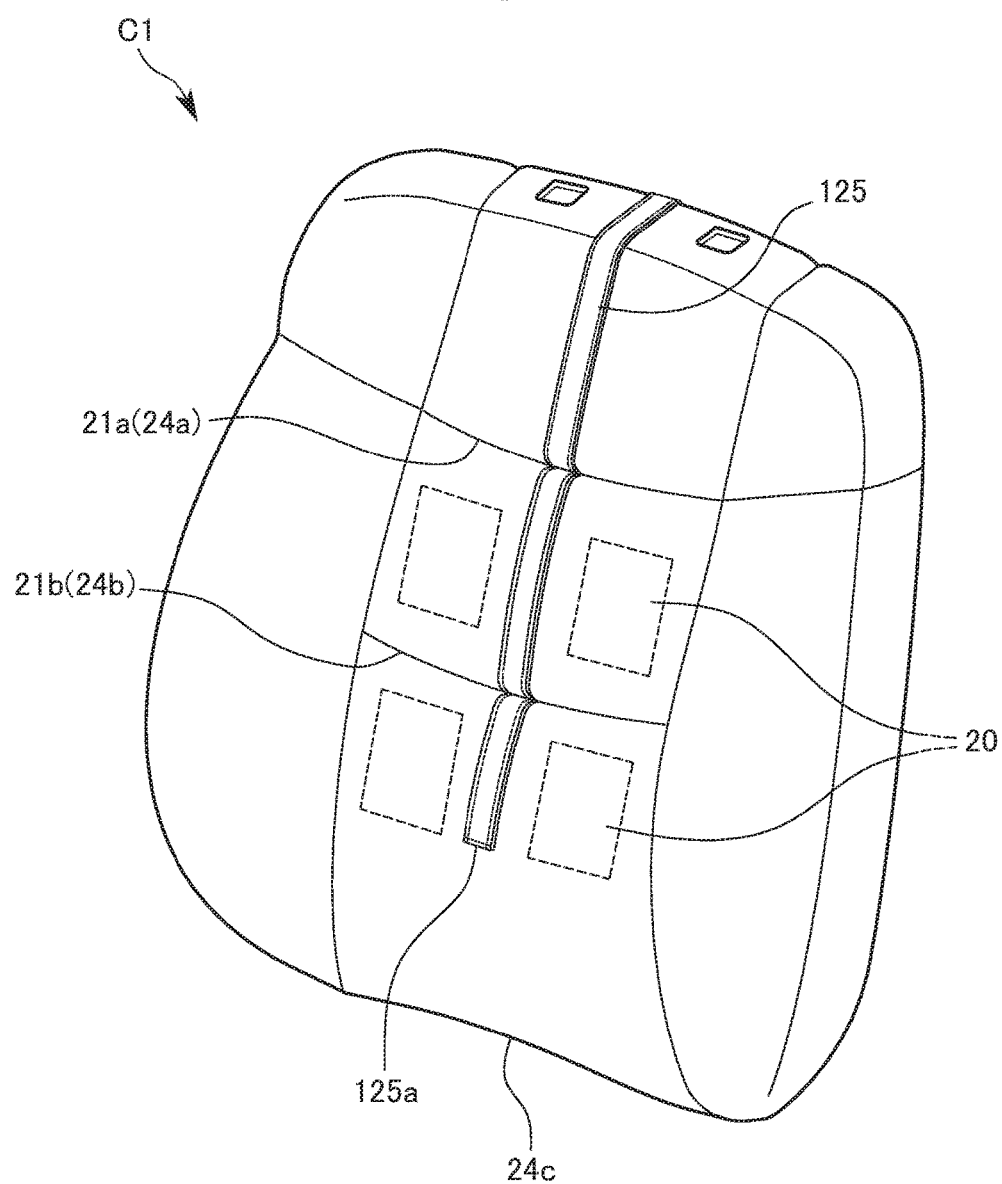
FIG. 14 is a perspective view of a seat back of a second embodiment of the present disclosure illustrating the arrangement position of conductive fabric.

Next, the arrangement position of conductive fabric of a second embodiment of the present disclosure is described with reference to FIG. 14. Note that in the description below, the contents overlapping with the above-described embodiment will not be repeatedly described in order to clarify feature differences.

The second embodiment is different from the first embodiment in the arrangement position of the conductive fabric. As illustrated in FIG. 14, conductive fabric 125 of the second embodiment in a belt shape having a width of about 20 mm is, on a substantially center portion of an outer surface of a skin 22 of a trim cover C2 in the seat width direction, disposed along the vertical direction connecting between a substantially middle point between a lower end portion of a seat back 2 and an insertion groove 21b and an upper end side of the seat back 2 attached to a headrest (not shown).

The lower end side of the conductive fabric 125 is sewn on the skin 22 of the trim cover C2, and the conductive fabric 125 extends from a lower end portion 125a thereof in the upward direction of the seat back 2 along the outer surface of the skin 22.

In the middle of extending toward the upper end side of the seat back 2, the conductive fabric 125 is, together with the skin 22 and a wadding 23, drawn into a sewn portion 24b and a sewn portion 24a, i.e., the insertion groove 21b and an insertion groove 21a. As in the first embodiment, the conductive fabric 125 and the skin 22 are sewn together at the sewn portions 24b, 24a with the conductive fabric 125 being bent in the insertion grooves 21b, 21a and being pulled out to the outer surface side of the skin 22 again. The conductive fabric 125 further extends through the sewn portions 24b, 24a in the upward direction of the seat back 2 along the outer surface of the skin 22.

The conductive fabric 125 is drawn into the seat back 2 from an upper end portion of a cushion pad P2, i.e., the position at an upper end of the seat back 2 when the trim cover C2 is attached. In other word, the conductive fabric 125 is drawn into the seat back 2 from the rear side of the headrest. The conductive fabric 125 has a bendable free end (not shown) further extending into the seat back 2 by a length of about 150 mm to about 200 mm.

As in the first embodiment, a J-hook 26 as a hooking tool is attached to the vicinity of a tip end portion of the free end of the conductive fabric 125. The free end of the conductive fabric 125 drawn into the seat back 2 partially contacts a seat frame F because the J-hook 26 is hooked onto part of the seat frame F. In the present embodiment, the J-hook 26 is hooked onto an upper frame 2b, and part of the conductive fabric 125 contacts the upper frame 2b to be electrically conductive with the upper frame 2b.

In the above-described first embodiment, the conductive fabric 25 is, together with the skin 22 and the wadding 23, drawn into the clearance between the seat back 2 and the seat cushion 1 from the position at the lower end of the seat back 2. However, the conductive fabric 125 may be, as in the second embodiment, drawn into the seat back 2 from above the seat back 2 to contact the seat frame F.

Third Embodiment

Figure 15:
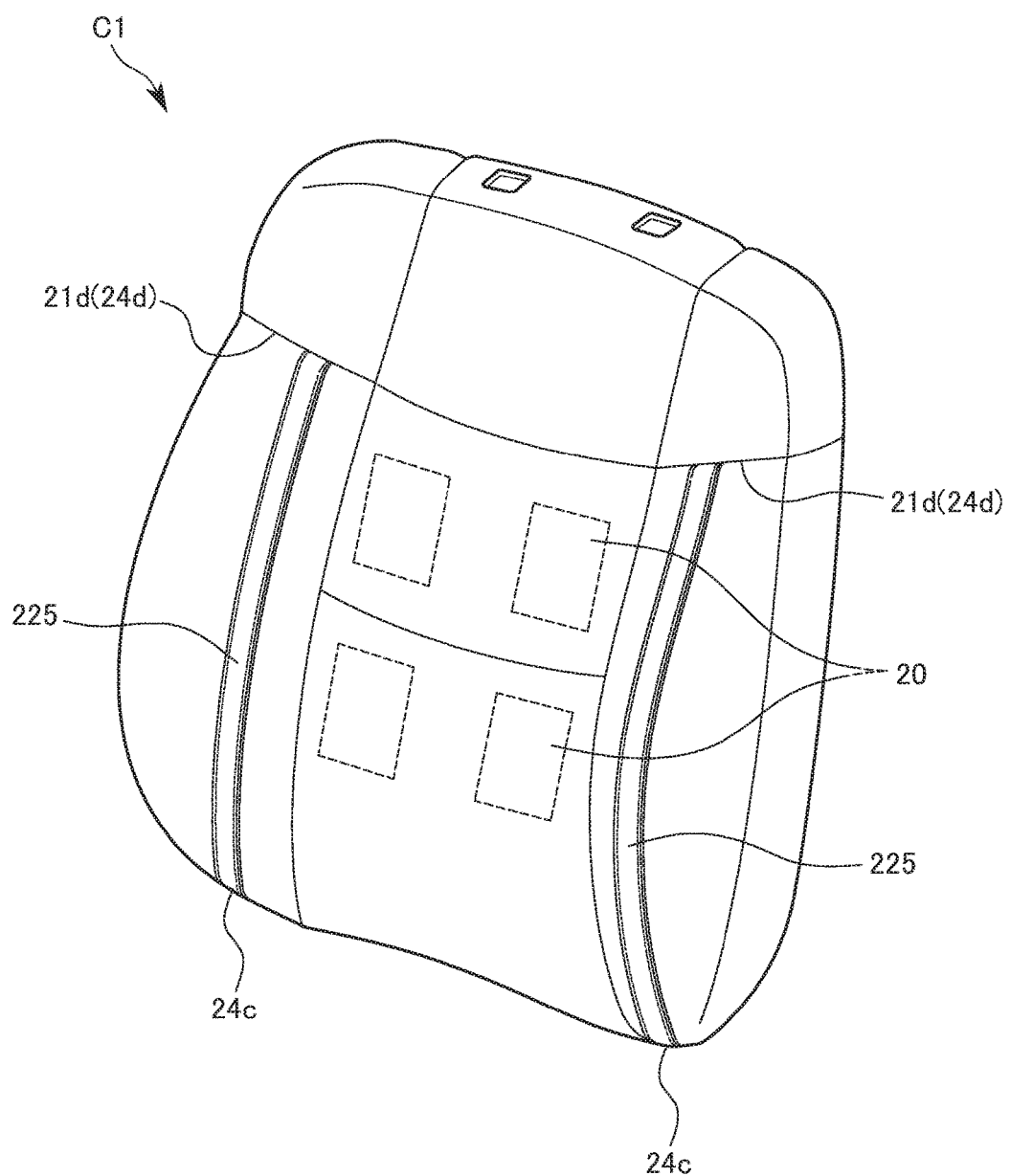
FIG. 15 is a perspective view of a seat back of a third embodiment of the present disclosure illustrating the arrangement position of conductive fabric.

Next, the arrangement position of conductive fabric of a third embodiment of the present disclosure is described with reference to FIG. 15. The third embodiment is different from the first embodiment in the arrangement position of the conductive fabric and in that a plurality of pieces of conductive fabric are arranged. As illustrated in FIG. 15, a single piece of conductive fabric 225 of the third embodiment (two pieces in total) in a belt shape having a width of about 20 mm is, in each of right and left side areas of an outer surface of a skin 22 of a trim cover C2, disposed in the vertical direction connecting between a sewn portion 24e along a diagonal insertion groove 21e formed on the upper side and the portion positioned at a lower end of a seat back 2.

The upper end side of the conductive fabric 225 is, together with the skin 22 and a wadding 23, drawn into the insertion groove 21e formed at a cushion pad P2 in a seat back 2 via the sewn portion 24e, and the conductive fabric 225, the skin 22, and the wadding 23 are sewn together at the sewn portion 24e. The conductive fabric 225 extends from the sewn portion 24e in the downward direction of the seat back 2 along the outer surface of the skin 22.

The conductive fabric 225 is, together with the skin 22 and the wadding 23, drawn into the clearance between the seat back 2 and a seat cushion 1 from a lower end portion of the cushion pad P2, i.e., the position at a lower end of the seat back 2 when the trim cover C2 is attached. The conductive fabric 225, the skin 22, and the wadding 23 are sewn together at a sewn portion 24c in the clearance. The conductive fabric 225 has a bendable free end (not shown) further extending into the seat back 2 from the sewn portion 24c by a length of about 150 mm to about 200 mm.

A J-hook 26 as a hooking tool is attached to the vicinity of a tip end portion of the free end of the conductive fabric 225. The free end of the conductive fabric 225 drawn into the clearance between the seat back 2 and the seat cushion 1 partially contacts a seat frame F because the J-hook 26 is hooked onto part of the seat frame F. In the present embodiment, the J-hook 26 is, as in the first embodiment, hooked onto a lower frame bridging portion 2d, part of the conductive fabric 225 contacts the lower frame bridging portion 2d, and the conductive fabric 225 and the seat frame F are in electrical conduction with each other through the lower frame bridging portion 2d.

Fourth Embodiment

Figure 16:
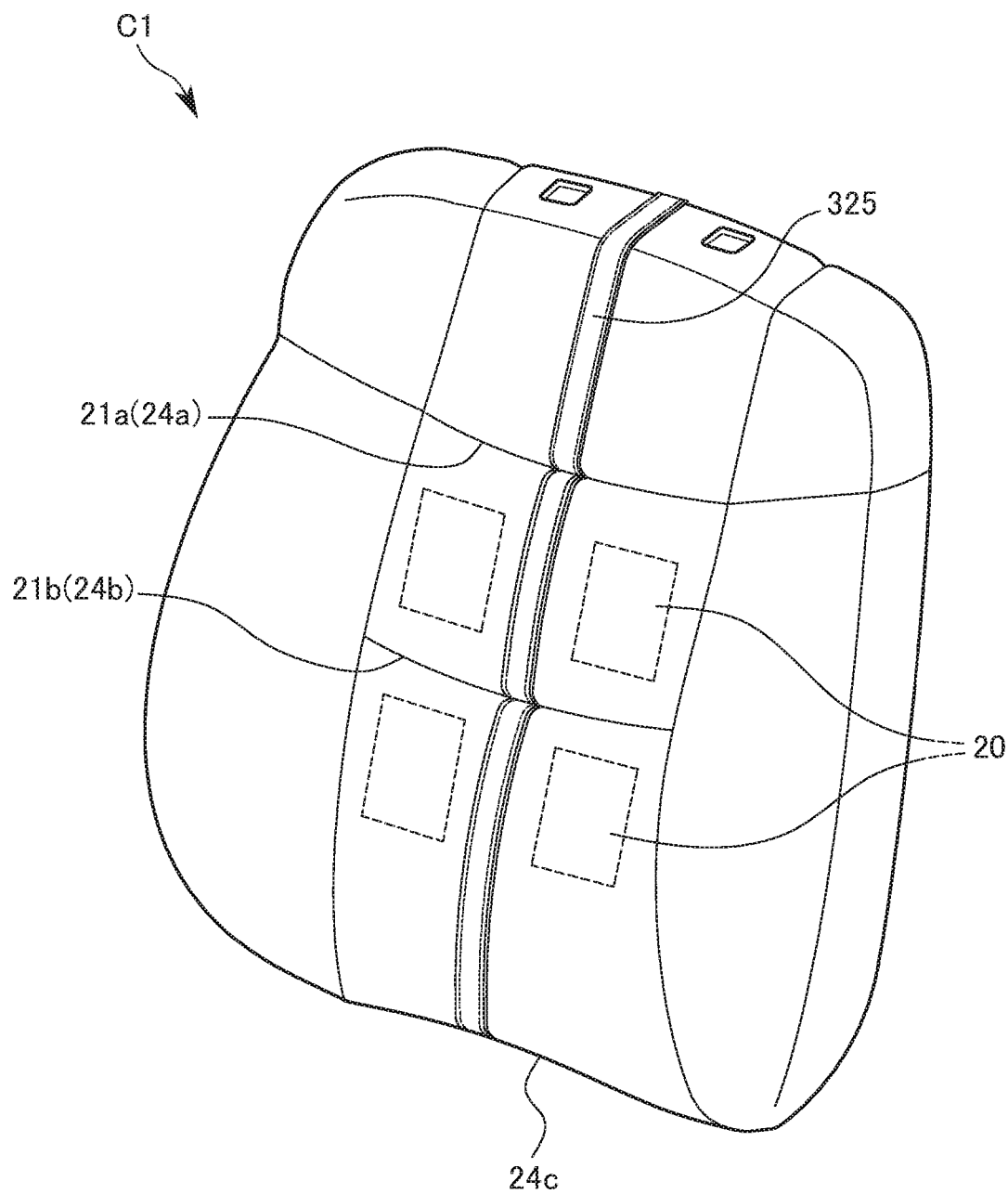
FIG. 16 is a perspective view of a seat back of a fourth embodiment of the present disclosure illustrating the arrangement position of conductive fabric.

Next, the arrangement position of conductive fabric of a fourth embodiment of the present disclosure is described with reference to FIG. 16. The fourth embodiment is different from the first embodiment in the arrangement position of the conductive fabric and in that the conductive fabric contacts a seat frame at both ends of the conductive fabric. As illustrated in FIG. 16, conductive fabric 325 of the fourth embodiment in a belt shape having a width of about 20 mm is, on a substantially center portion of an outer surface of a skin 22 of a trim cover C2 in the seat width direction, disposed in the vertical direction connecting between an upper end position of a seat back 2 attached to a headrest (not shown) and a sewn portion 24c formed on the lower side and positioned at a lower end of the seat back 2 when a cushion pad P2 is covered.

The conductive fabric 325 is drawn into the seat back 2 from an upper end portion of the cushion pad P2, i.e., the position at an upper end of the seat back 2 when the trim cover C2 is attached. In other word, the conductive fabric 325 is drawn into the seat back 2 from the rear side of the headrest. The conductive fabric 325 has a bendable free end further extending into the seat back 2 by a length of about 150 mm to about 200 mm. The conductive fabric 325 further extends from the position, at which the conductive fabric 325 is drawn into the seat back 2, in the downward direction of the seat back 2 along the outer surface of the skin 22.

As described above, the conductive fabric 325 is sewn on the outer surface of the trim cover C, and the conductive fabric 325, the skin 22, and a wadding 23 are together drawn into sewn portions 24a, 24b, i.e., insertion grooves 21a, 21b, in the middle of extending toward the lower end of the seat back 2. As in the first embodiment, the conductive fabric 325, the skin 22, and the wadding 23 are sewn together at the sewn portions 24b, 24a with the conductive fabric 325 being bent in the insertion grooves 21b, 21a and being pulled out to the outer surface side of the skin 22 again. The conductive fabric 325 further extends through the sewn portions 24a, 24b in the downward direction of the seat back 2 along the outer surface of the skin 22.

The conductive fabric 325 is, together with the skin 22 and the wadding 23, drawn into the clearance between the seat back 2 and a seat cushion 1 from a lower end portion of the cushion pad P2, i.e., the position at the lower end of the seat back 2 when the trim cover C2 is attached. The conductive fabric 325, the skin 22, and the wadding 23 are sewn together at the sewn portion 24c in the clearance. The conductive fabric 325 has a bendable free end further extending into the seat back 2 from the sewn portion 24c by a length of about 150 mm to about 200 mm.

In the fourth embodiment, the free ends are formed respectively at both of the upper and lower ends of the conductive fabric 325. A J-hook 26 as a hooking tool is attached to the vicinity of a tip end portion of each free end. Each free end of the conductive fabric 325 drawn into the seat back 2 partially contacts a seat frame F because the J-hook 26 is hooked onto part of the seat frame F.

As in the second embodiment, the J-hook 26 attached to the upper free end is hooked onto an upper frame 2b, and part of the conductive fabric 325 contacts the upper frame 2b. Thus, the conductive fabric 325 and the upper frame 2b have electrical conductivity with each other. On the other hand, the J-hook 26 attached to the lower free end is, as in the first embodiment, hooked onto a lower frame bridging portion 2d, and part of the conductive fabric 325 contacts the lower frame bridging portion 2d. Thus, the conductive fabric 325 and the lower frame bridging portion 2d have electrical conductivity with each other. As in the fourth embodiment, the conductive fabric 325 is drawn into the seat back 2 from both of the upper and lower sides of the seat back 2 so that both ends of the conductive fabric 325 can contact the seat frame F.

Fifth Embodiment

Figure 17:
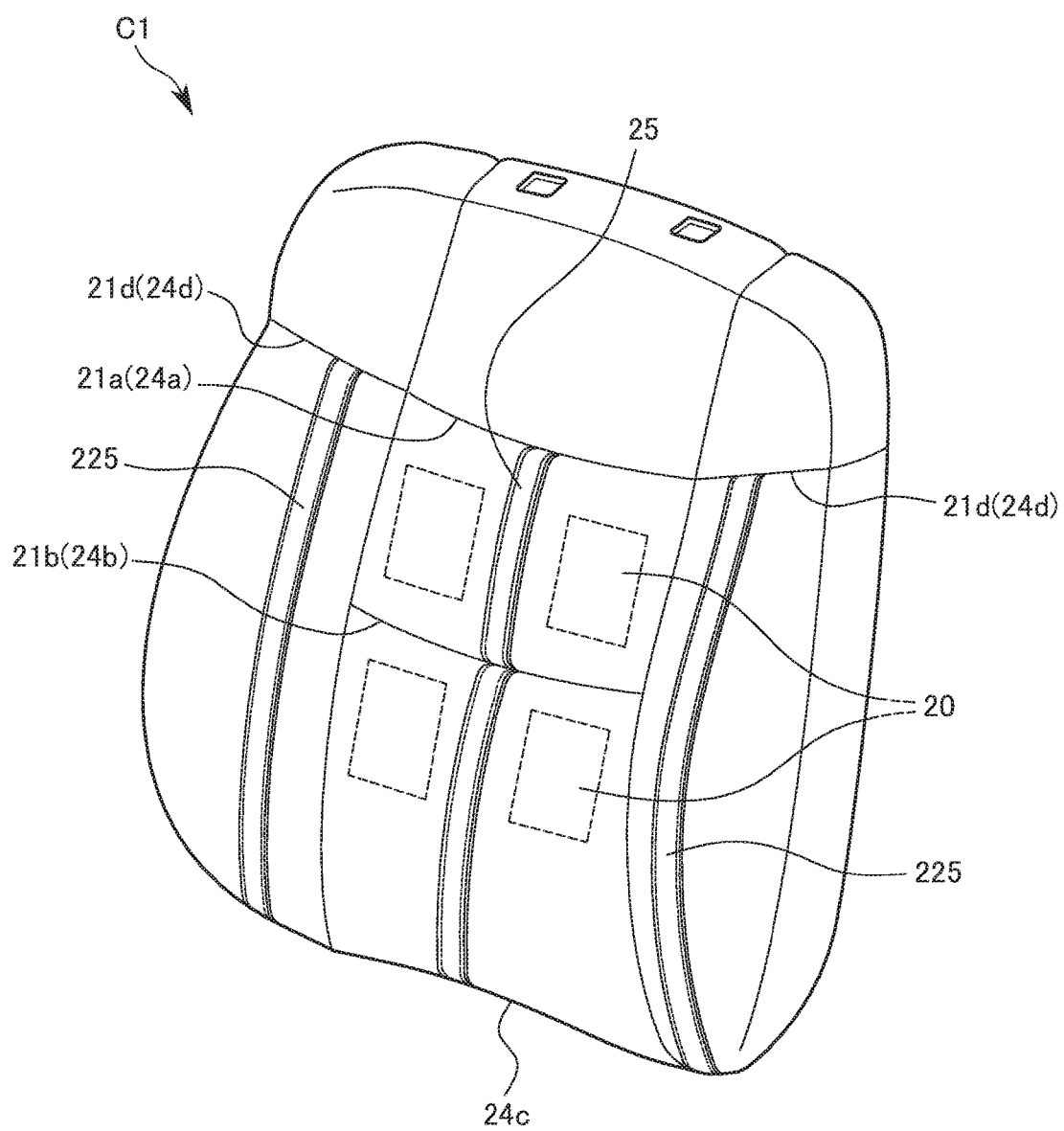
FIG. 17 is a perspective view of a seat back of a fifth embodiment of the present disclosure illustrating the arrangement position of conductive fabric.

Next, the arrangement position of conductive fabric of a fifth embodiment of the present disclosure is described with reference to FIG. 17. In the fifth embodiment, the above-described first and third embodiments are combined together, and a plurality of pieces of conductive fabric is arranged. The configuration and arrangement of conductive fabric 25, 225 and the method for contacting a seat frame F and the conductive fabric 25, 225 together are similar to those described above.

Sixth Embodiment

Figure 18:
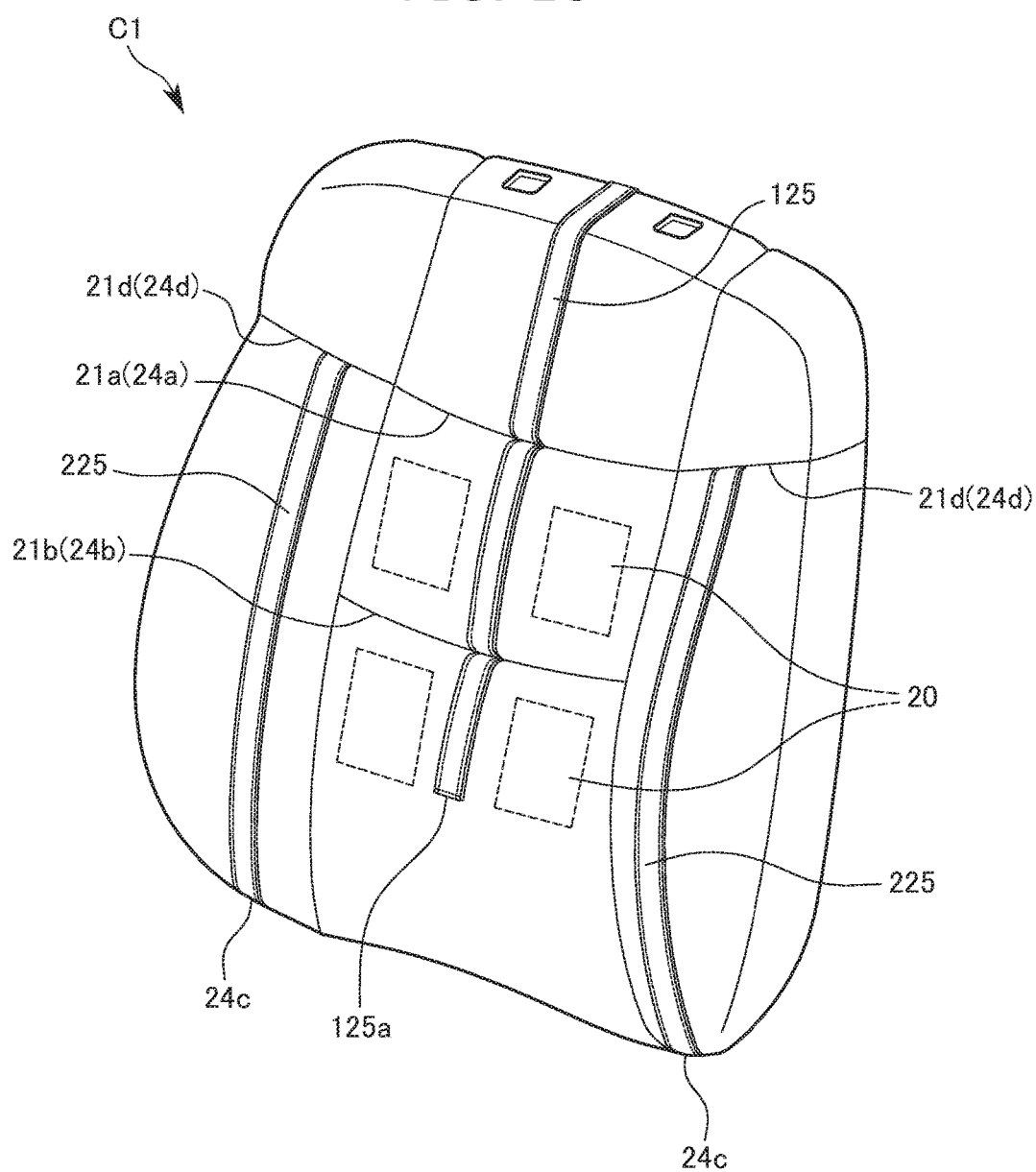
FIG. 18 is a perspective view of a seat back of a sixth embodiment of the present disclosure illustrating the arrangement position of conductive fabric.

Next, the arrangement position of conductive fabric of a sixth embodiment of the present disclosure is described with reference to FIG. 18. In the sixth embodiment, the above-described second and third embodiments are combined together, and a plurality of pieces of conductive fabric is arranged. The configuration and arrangement of conductive fabric 125, 225 and the method for contacting a seat frame F and the conductive fabric 125, 225 together are similar to those described above.

Seventh Embodiment

Figure 19:
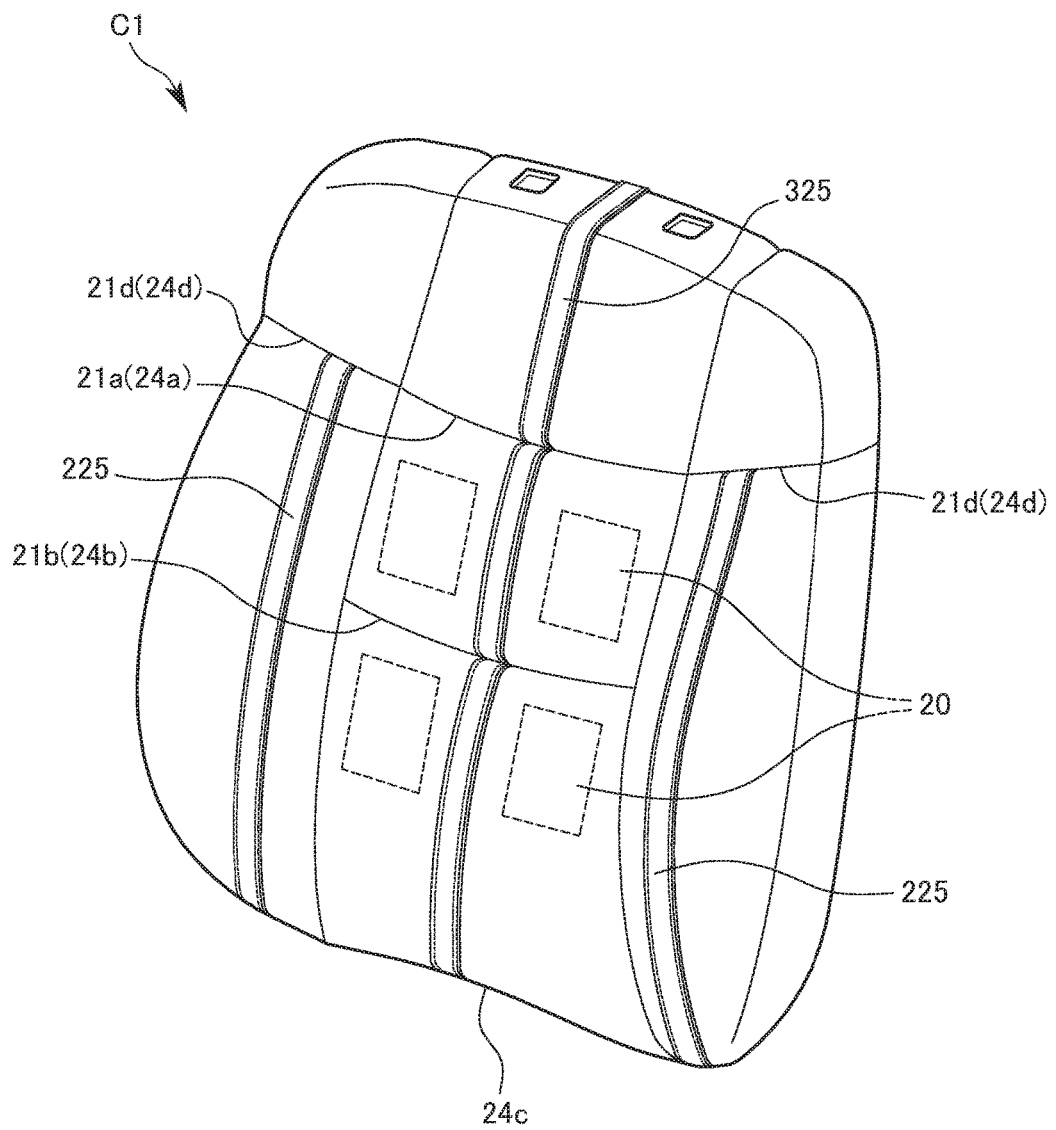
FIG. 19 is a perspective view of a seat back of a seventh embodiment of the present disclosure illustrating the arrangement position of conductive fabric.

Next, the arrangement position of conductive fabric of a seventh embodiment of the present disclosure is described with reference to FIG. 19. In the seventh embodiment, the above-described third and fourth embodiments are combined together, and a plurality of pieces of conductive fabric is arranged. The configuration and arrangement of conductive fabric 225, 325 and the method for contacting a seat frame F and the conductive fabric 225, 325 together are similar to those described above.

Eighth Embodiment

Next, the arrangement position of conductive fabric of an eighth embodiment of the present disclosure is described with reference to FIG. 20. The eighth embodiment is different from the first embodiment in the arrangement position of the conductive fabric and in that the conductive fabric contacts a seat frame not from the upper and lower sides of a seat but from the right and left sides of the seat.

Figure 20:
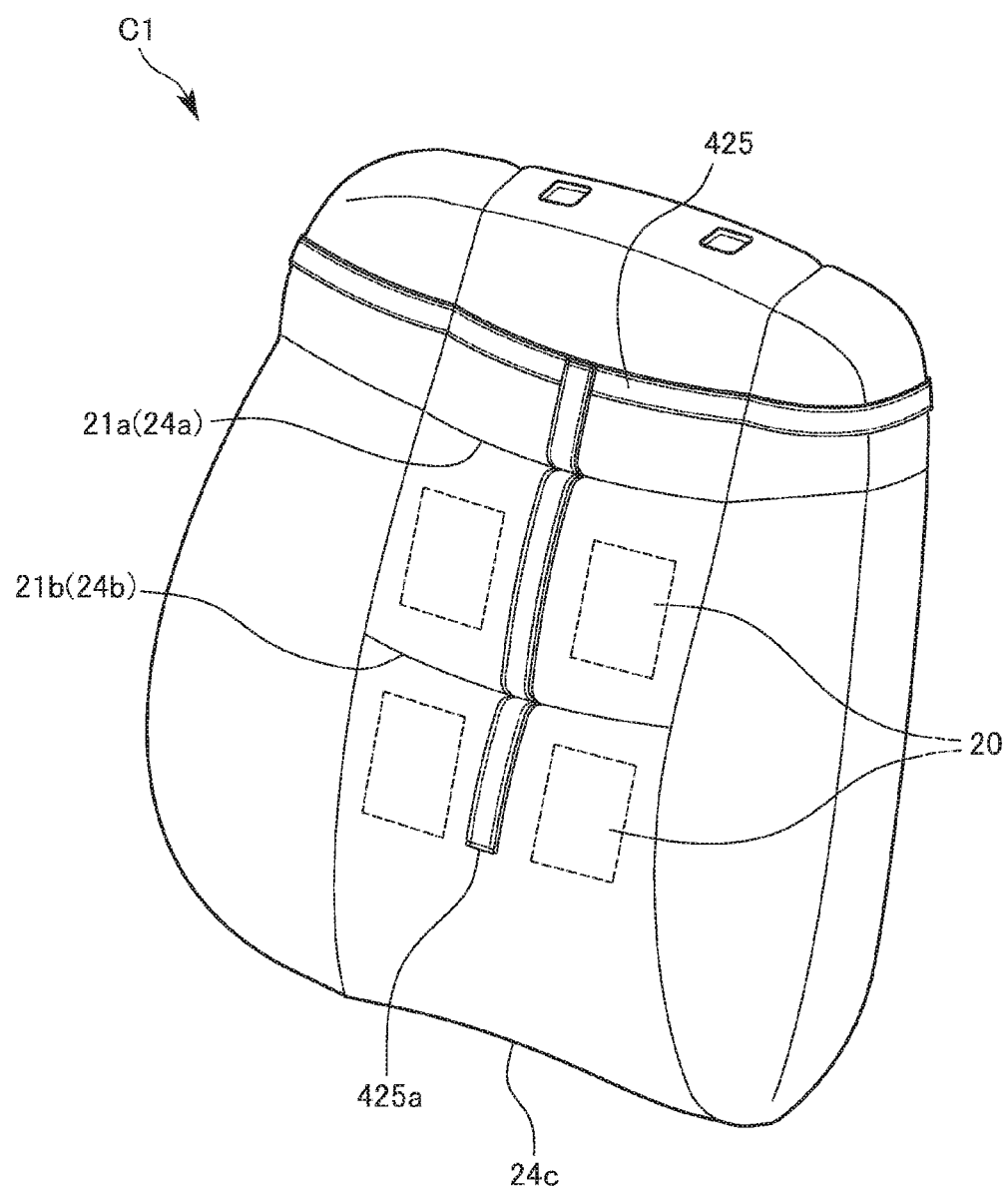
FIG. 20 is a perspective view of a seat back of an eighth embodiment of the present disclosure illustrating the arrangement position of conductive fabric.

As illustrated in FIG. 20, conductive fabric 425 of the eighth embodiment in a belt shape having a width of about 20 mm is, on a substantially center portion of an outer surface of a skin 22 of a trim cover C2 in the seat width direction, disposed in the vertical direction connecting between a substantially middle point between a lower end portion of a seat back 2 and an insertion groove 21b and a substantially middle point between an insertion groove 21a and an upper end portion of the seat back 2. Moreover, another piece of conductive fabric 425 in a belt shape having a width of about 20 mm is, at the substantially middle point between the insertion groove 21a and the upper end portion of the seat back 2, disposed in the transverse direction toward both of right and left ends of the seat back 2.

The conductive fabric 425 is drawn into the seat back 2 from each of right and left end portions of a cushion pad P2, i.e., each of the positions at the right and left ends of the seat back 2 when the trim cover C2 is attached. The conductive fabric 425 has bendable free ends (not shown) further extending into the seat back 2 by a length of about 150 mm to about 200 mm.

In the present embodiment, as in the above-described first embodiment, a J-hook 26 as a hooking tool is attached to the vicinity of a tip end portion of each free end of the conductive fabric 425. Each free end of the conductive fabric 425 drawn into the seat back 2 partially contacts a seat frame F because the J-hook 26 is hooked onto part of the seat frame F. In the present embodiment, the J-hook 26 drawn into the seat back 2 from each of the right and left ends thereof is hooked onto an upper frame 2b (or a side frame 2a), part of the conductive fabric 425 contacts the upper frame 2b, and the conductive fabric 425 and the upper frame 2b have electrical conductivity with each other.

In the above-described first embodiment, the conductive fabric 25 is, together with the skin 22 and the wadding 23, drawn into the clearance between the seat back 2 and the seat cushion 1 from the position at the lower or upper end of the seat back 2. However, as in the eighth embodiment, the conductive fabric 425 is drawn into the seat back 2 from the right and left sides of the seat back 2 so that the conductive fabric 425 can contact the seat frame F. Note that in the case where the conductive fabric 425 contacts the seat frame F from the right and left sides of the seat back 2 as in the present embodiment, the conductive fabric 425 may be provided on at least one of the right and left sides. That is, the conductive fabric 425 may be drawn into the seat back 2 from either one of the right and left sides of the seat back 2.

Ninth Embodiment

Next, the arrangement position of conductive fabric of a ninth embodiment of the present disclosure is described with reference to FIG. 21. The ninth embodiment is different from the first embodiment in the arrangement position and number of the conductive fabric and in that the conductive fabric contacts a seat frame not from the upper and lower sides of a seat but from the right and left sides of the seat.

Figure 21:
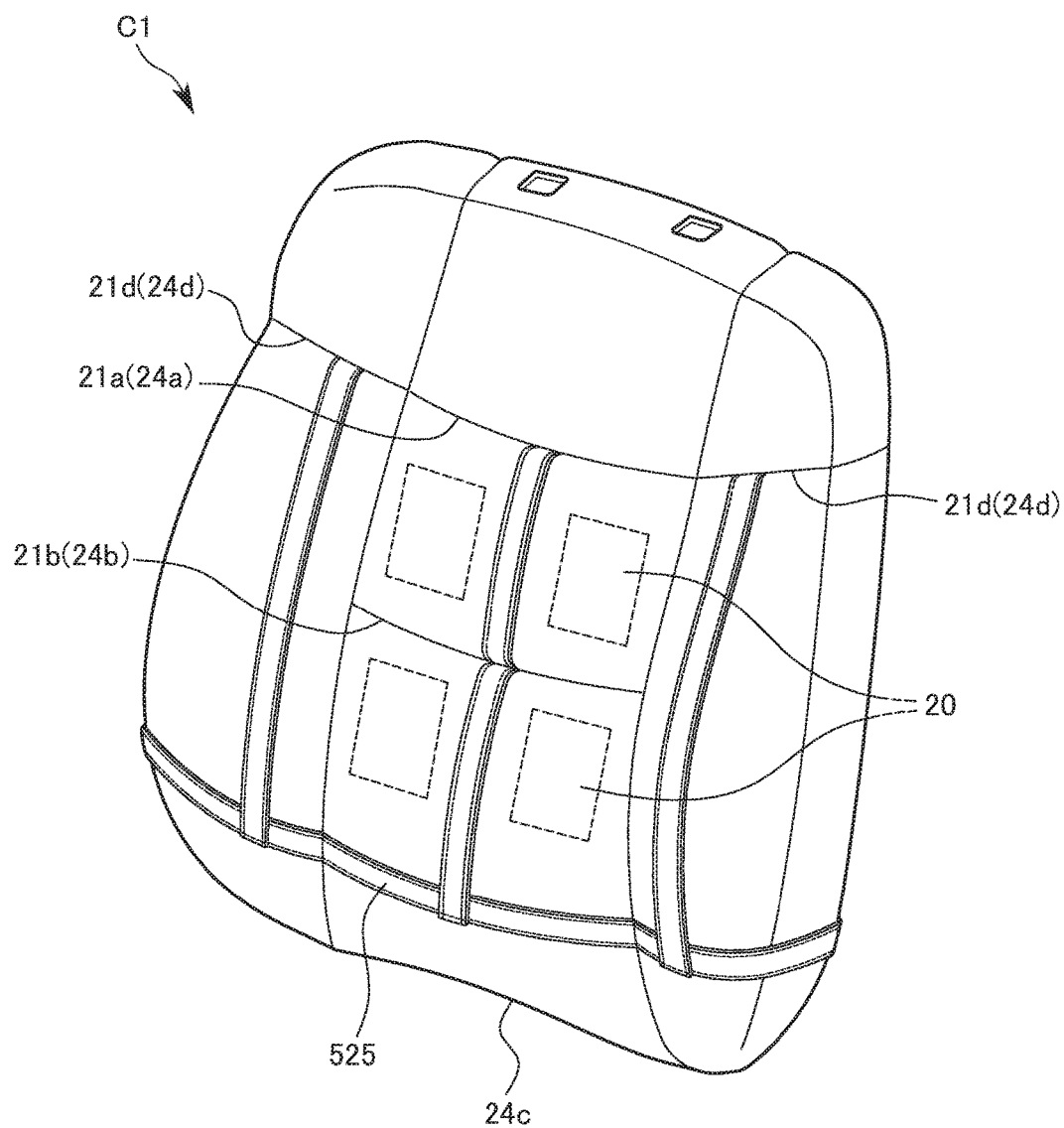
FIG. 21 is a perspective view of a seat back of a ninth embodiment of the present disclosure illustrating the arrangement position of conductive fabric.

As illustrated in FIG. 21, conductive fabric 525 of the ninth embodiment in a belt shape having a width of about 20 mm is, on a substantially center portion of an outer surface of a skin 22 of a trim cover C2 in the seat width direction, disposed in the vertical direction connecting between a sewn portion 24a along a transverse insertion groove 21a formed on the upper side and a substantially middle point between a lower end portion of a seat back 2 and an insertion groove 21b. Moreover, another piece of conductive fabric 525 (two pieces in total) in a belt shape having a width of about 20 mm is, in each of right and left side areas of the outer surface of the skin 22 of the trim cover C2, disposed in the vertical direction connecting between a sewn portion 24e along a diagonal insertion groove 21e formed on the upper side and the substantially middle point between the lower end portion of the seat back 2 and the insertion groove 21b. Further, still another piece of conductive fabric 525 in a belt shape having a width of about 20 mm is, at the substantially middle point between the insertion groove 21b and the lower end portion of the seat back 2, disposed in the transverse direction toward both of right and left ends of the seat back 2.

The conductive fabric 525 is drawn into the seat back 2 from each of right and left end portions of a cushion pad P2, i.e., each of the positions at the right and left ends of the seat back 2 when the trim cover C2 is attached. The conductive fabric 525 has bendable free ends (not shown) further extending into the seat back 2 by a length of about 150 mm to about 200 mm.

In the present embodiment, as in the above-described first embodiment, a J-hook 26 as a hooking tool is attached to the vicinity of a tip end portion of each free end of the conductive fabric 525. Each free end of the conductive fabric 525 drawn into the seat back 2 partially contacts a seat frame F because the J-hook 26 is hooked onto part of the seat frame F. In the present embodiment, the J-hook 26 drawn into the seat back 2 from each of the right and left ends thereof is hooked onto a side frame 2a, part of the conductive fabric 525 contacts the side frame 2a, and the conductive fabric 525 and the side frame 2a are in electrical conduction with each other.

In the ninth embodiment, the conductive fabric 525 is, as in the above-described eighth embodiment, drawn into the seat back 2 from the right and left sides of the seat back 2 so that the conductive fabric 525 can contact the seat frame F. Note that in the case where the conductive fabric 525 contacts the seat frame F from the right and left sides of the seat back 2 as in the present embodiment, the conductive fabric 525 may be provided on at least one of the right and left sides. That is, the conductive fabric 525 may be drawn into the seat back 2 from either one of the right and left sides of the seat back 2.

The present disclosure has been specifically described above with reference to the embodiments and the variations thereof, but is not limited to the above-described embodiments and the variations thereof. Various changes such as combination of features can be made without departing from the gist of the present disclosure.

For example, as long as the conductive fabric 25 is disposed on the surface portion of the seat back 2 contacting the seated passenger and contacts, at one or both ends thereof, the seat frame F to be electrically conductive with the seat frame F, other variations in the arrangement position of the conductive fabric 25 and the contact position between the conductive fabric 25 and the seat frame F can be made except for the aspects of the above-described embodiments.

In the above-described embodiments, the ground electrode 10 and the sheet-shaped sensors 20 have been described as being formed of the conductive fabric tapes, but are not limited to the conductive fabric tapes. The conductive fabric tapes are optionally changeable to a metal conductor as long as the metal conductor has electrical conductivity. Examples of the metal conductor include conductive fibers etc.

In the above-described embodiments, each sheet-shaped sensor 20 includes a conductive line forming a sensor body, and a conductive sheet protecting the conductive line. However, the sheet-shaped sensor 20 is not limited to such a configuration. Each sheet-shaped sensor 20 may include only the conductive sheet without the conductive line. Note that, e.g., gold paste, silver paste, or copper paste having a high conductivity can be used for the conductive line, and, e.g., carbon paste resistive to oxidation and having conductivity can be used for the conductive sheet.

In the above-described embodiments, the sheet-shaped sensors 20 are arranged between the cushion pad P2 and the skin 22, but are not limited to such a configuration. For example, the sheet-shaped sensors 20 may be attached to the skin 22. In the above-described embodiments, the number of sheet-shaped sensors 20 is four, but is not limited to such a number. The number of sheet-shaped sensors 20 is optionally adjustable considering the balance between stability in potential difference detection and a manufacturing cost. Moreover, all of the sheet-shaped sensors 20 have the same size, and are arranged at equal intervals. However, the sheet-shaped sensors 20 are not limited to such a configuration. Each of the sizes of the first sensor 20*a*, the second sensor 20*b*, the third sensor 20*c*, and the fourth sensor 20*d* may be changed, and the arrangement positions of these sensors may be changed. For example, the second sensor 20*b* may be disposed above the first sensor 20*a*.

In the above-described embodiments, the heart rate measurement device 3 includes, as a component, the display D showing the electrocardiographic waveform, but may further include a vibration motor for maintaining the seated passenger at an awakening state, a transmitter for generating an alarm, or a light emitter for emitting light. Further, the vehicle seat S of the present disclosure can be utilized for the purpose of monitoring a passenger having a heart problem. In this case, the display D is preferably disposed at such a position that a passenger(s) other than the passenger having the heart problem can monitor the working condition of the heart. In addition, a vibration motor may be provided at a seat other than the seat provided with the heart rate measurement device 3. When a decline in the function of the heart is detected, such a seat may vibrate to report to other passenger(s).

In the above-described embodiments, the person with a height of 150 cm has been described as an example of the seated passenger assumed as being physically small, and the person with a height of 190 cm has been described as an example of the seated passenger assumed as being physically big. However, such assumption is optional. For example, in the case of assuming only seating of an adult American or assuming only seating of a child, a reference physique may be set according to such assumption. Similar advantageous effects can be provided in the following manner. The positions of the sheet-shaped sensors 20 are determined such that in the state in which a passenger with the reference physique is seated and faces forward of the seat back 2, the sheet-shaped sensors 20 sandwich the heart of the passenger.

In the above-described embodiments, the mountable vehicle seat used for automobiles has been described as a specific example, but the present disclosure is not limited to such a vehicle seat. The vehicle seat can be utilized not only as vehicle seats of trains and buses but also as vehicle seats of airplanes and ships, for example.

In the above-described embodiments, the vehicle seat S of the present disclosure has been generally described. Note that the above-described embodiments have been set forth merely as examples for the sake of easy understanding of the present disclosure, and are not intended to limit the present disclosure. Changes and modifications can be made without departing from the gist of the present disclosure. The present disclosure includes equivalents thereof. In particular, the shape, arrangement, configuration of the sheet-shaped sensors 20 attached to the cushion pad P2 forming the seat back 2 have been described merely as examples in the above-described embodiments, and are not intended to limit the present disclosure.

| TABLE OF REFERENCE NUMERALS | |
|---|---|
| S: | vehicle seat |
| F: | seat frame |
| P: | cushion pad |
| C: | trim cover |
| L: | reclining mechanism |
| | L1: reclining shaft |
| 1: | seat cushion |
| | F1: seat cushion frame |
| | P1: cushion pad |
| | C1: trim cover |
| | 1a: frame |
| | 1b: connection pipe |
| | 1c: S-spring |
| 2: | seat back |
| | F2: seat back frame |
| | P2: cushion pad |
| | C2: trim cover |
| | 2a: side frame |
| | 2b: upper frame |
| | 2c: lower frame base (member side) |
| | 2d: lower frame bridging portion (member center) |
| | 2e: pressure receiving member |
| | 2f: wire |
| 3: | heart rate measurement device |
| 10: | ground electrode |
| 20: | sheet-shaped sensor |
| | 20a: first sensor |
| | 20b: second sensor |
| | 20c: third sensor |
| | 20d: fourth sensor |
| 21: | insertion groove (21a to 21d) |

-continued

TABLE OF REFERENCE NUMERALS

| | |
|---|---|
| 22: | skin |
| 23: | wadding |
| 24: | sewn portion (24a to 24d) |
| 25: | conductive fabric |
| | 25a: seam allowance |
| 26: | J-hook |
| | 26a: attachment portion |
| | 26b: hooking portion |
| 27: | sewing thread |
| 30: | instrumentation amplifier |
| 31, 32, 33: | operational amplifier |
| 40: | DC component removal circuit |
| 41: | capacitor |
| 50: | inverting amplifier |
| 60: | passband filter |
| 70: | A/D converter circuit |
| 80: | arithmetic device |
| 81: | CPU |
| 82: | RAM |
| | 82a: storage |
| 83: | ROM |
| | 83a: waveform generator |
| | 83b: selector |
| D: | display |
| V1, V2: | voltage waveform data |
| VH: | electrocardiographic waveform data |
| N: | noise |

The invention claimed is:

1. A vehicle seat comprising:
a seat that comprises a seat frame having electrical conductivity, a cushion pad, and a trim cover that covers the seat frame and the cushion pad;
a sensor that is attached to the seat and detects an electric signal associated with a biopotential of a seated passenger; and
a central processing unit configured to measure a heart rate of the seated passenger based on the electric signal detected by the sensor,
wherein at least a part of the trim cover is provided with a conductive member disposed on a surface of the trim cover configured to contact the seated passenger,
wherein a part of the conductive member contacts the seat frame, whereby the conductive member and the seat frame are in electrical conduction with each other, and
wherein the sensor comprises a plurality of sensors provided at a respective plurality of portions of the trim cover, and
the conductive member is disposed at a position not overlapping with the plurality of sensors, and is provided between the plurality of sensors.

2. The vehicle seat according to claim 1,
wherein the at least a part of the trim cover is formed of a skin and a wadding material, and
wherein the wadding material is disposed between the skin and the sensor.

3. The vehicle seat according to claim 1,
wherein the conductive member comprises a conductive fabric, and
wherein the conductive fabric is sewn on the trim cover.

4. The vehicle seat according to claim 1,
wherein the conductive member has a free end on a side contacting the seat frame,
wherein the vehicle seat further comprises a hook-shaped member that is attached to the free end, and
wherein the conductive member is drawn into the seat, and the hook-shaped member is hooked onto the seat frame, whereby the conductive member and the seat frame contact each other.

5. The vehicle seat according to claim 1, wherein the sensor is a capacitance-coupled sheet-shaped sensor.

6. The vehicle seat according to claim 1, wherein
the plurality of sensors are provided on each of right and left sides of the seat, and
the conductive member is provided along a longitudinal direction of the seat.

7. The vehicle seat according to claim 6, wherein the conductive member is provided at a center of the seat in a width direction of the seat.

8. The vehicle seat of claim 6, wherein the conductive member extends around an end portion of the seat in the longitudinal direction of the seat toward a rear side of the seat.

9. The vehicle seat according to claim 6, wherein the conductive member outwardly extends beyond an end portion of the sensor in a longitudinal direction of the sensor.

10. The vehicle seat according to claim 6, wherein the conductive member outwardly extends beyond first and second end portions of the sensor in a longitudinal direction of the sensor.

11. The vehicle seat according to claim 6,
wherein the conductive member comprises a first conductive member that extends along the longitudinal direction of the seat, and a second conductive member that extends along a width direction of the seat, and
wherein the first and second conductive members are electrically connected to each other.

12. The vehicle seat according to claim 11, wherein the second conductive member extends around an end portion of the seat in the width direction of the seat toward a rear side of the seat.

* * * * *